United States Patent
Yu et al.

(10) Patent No.: US 11,242,530 B2
(45) Date of Patent: Feb. 8, 2022

(54) SIRNA KNOCKING DOWN HUMAN PD-1 AND RECOMBINANT EXPRESSION CAR-T VECTOR AND THEIR CONSTRUCTION METHODS AND APPLICATIONS

(71) Applicant: SHANGHAI UNICAR-THERAPY BIO-MEDICINE TECHNOLOGY CO., LTD, Shanghai (CN)

(72) Inventors: Lei Yu, Shanghai (CN); Liqing Kang, Shanghai (CN); Zhou Yu, Shanghai (CN)

(73) Assignee: SHANGHAI UNICAR-THERAPY BIO-MEDICINE TECHNOLOGY CO., LTD, Shanghai (CN)

( * ) Notice: Subject to any disclaimer, the term of this patent is extended or adjusted under 35 U.S.C. 154(b) by 293 days.

(21) Appl. No.: 16/331,147

(22) PCT Filed: Nov. 13, 2017

(86) PCT No.: PCT/CN2017/110653
§ 371 (c)(1),
(2) Date: Mar. 7, 2019

(87) PCT Pub. No.: WO2018/103501
PCT Pub. Date: Jun. 14, 2018

(65) Prior Publication Data
US 2019/0218559 A1  Jul. 18, 2019

(30) Foreign Application Priority Data
Dec. 8, 2016 (CN) .......................... 201611123283.4

(51) Int. Cl.
*C12N 15/113* (2010.01)
*C12N 15/86* (2006.01)
(Continued)

(52) U.S. Cl.
CPC .......... *C12N 15/1138* (2013.01); *A61K 35/17* (2013.01); *C07K 14/70521* (2013.01);
(Continued)

(58) Field of Classification Search
CPC .... C12N 15/1138; C12N 15/66; C12N 15/86; C12N 2310/14; C12N 2310/531;
(Continued)

(56) References Cited

U.S. PATENT DOCUMENTS 6,623,940 B1 * 9/2003 Ledbetter ............. C07K 14/005
435/320.1
9,273,141 B2 * 3/2016 Algate ................ C07K 16/2803
(Continued)

FOREIGN PATENT DOCUMENTS

CN      104711253 A  *  6/2015
CN      106191062 A     12/2016
(Continued)

OTHER PUBLICATIONS

Borkner L, Kaiser A, van de Kasteele W, Andreesen R, Mackensen A, Haanen JB, Schumacher TN, Blank C. RNA interference targeting programmed death receptor-1 improves immune functions of tumor-specific T cells. Cancer immunology, immunotherapy. Aug. 2010;59(8):1173-83. (Year: 2010).*
(Continued)

*Primary Examiner* — Kevin K Hill
*Assistant Examiner* — Anjeanette Roberts
(74) *Attorney, Agent, or Firm* — Bayramoglu Law Offices LLC

(57) ABSTRACT

Provided are a human PD-1 knockdown siRNA, a recombinant expression CAR-T vector, a preparation method thereof, and an application of the same. A PD-1 knockdown siRNA expression cassette and an siRNA expression product thereof can be applied to a CAR-T therapy of multiple
(Continued)

myeloma (MM) for eliminating or alleviating a tumor immune escape mechanism, and in the suppression of an immune escape mechanism in a CAR-T therapy of a tumor, such as pancreatic cancer, brain glioma, and myeloma.

19 Claims, 8 Drawing Sheets

Specification includes a Sequence Listing.

(51) Int. Cl.
    *A61K 35/17*     (2015.01)
    *C12N 15/66*     (2006.01)
    *C07K 14/705*     (2006.01)

(52) U.S. Cl.
    CPC .............. *C12N 15/66* (2013.01); *C12N 15/86* (2013.01); *C12N 2310/14* (2013.01); *C12N 2310/531* (2013.01); *C12N 2320/32* (2013.01); *C12N 2330/51* (2013.01); *C12N 2740/15043* (2013.01); *C12N 2740/15051* (2013.01); *C12N 2740/16043* (2013.01)

(58) Field of Classification Search
    CPC ............ C12N 2320/32; C12N 2330/51; C12N 2740/15043; C12N 2740/15051; C12N 2740/16043; A61K 35/17; C07K 14/70521
See application file for complete search history.

(56) References Cited

U.S. PATENT DOCUMENTS

| | | | | |
|---|---|---|---|---|
| 9,624,276 | B2 * | 4/2017 | Young ................ | C07K 16/2887 |
| 10,385,319 | B2 * | 8/2019 | Puckette .............. | G01N 33/573 |
| 2013/0323302 | A1 * | 12/2013 | Constable ............ | C07K 16/081 424/450 |
| 2015/0225480 | A1 * | 8/2015 | Powell, Jr. ......... | C07K 16/2803 424/184.1 |
| 2015/0368342 | A1 * | 12/2015 | Wu ....................... | C07K 16/18 424/134.1 |
| 2016/0199412 | A1 * | 7/2016 | Tareen .................. | C12N 15/86 424/93.71 |

FOREIGN PATENT DOCUMENTS

| | | | | |
|---|---|---|---|---|
| CN | 107058315 | A | 8/2017 | |
| JP | 2004180561 | A * | 7/2004 | .............. C12Q 1/689 |
| WO | WO-2012079000 | A1 * | 6/2012 | .............. A61P 37/02 |
| WO | 2015023553 | A3 | 4/2015 | |
| WO | WO-2015142661 | A1 * | 9/2015 | .............. C07K 16/28 |
| WO | WO-2016132122 | A1 * | 8/2016 | ........... C12Q 1/6897 |
| WO | WO-2017207979 | A1 * | 12/2017 | ........... C12N 9/1205 |

OTHER PUBLICATIONS

Naito Y, Ui-Tei K. siRNA design software for a target gene-specific RNA interference. Frontiers in genetics. Jun. 11, 2012;3:102. (Year: 2012).*

Miyagishi M, Taira K. Development and application of siRNA expression vector. InNucleic acids symposium series Nov. 2002 (vol. 2 , No. 1, pp. 113-114). Oxford University Press. (Year: 2002).*
SBI System Biosciences; MicroRNA Precursor Constructs; Cat.#s PMIRHxxxPA-1; version Feb. 28, 2008 (Year: 2008).*
Guan LZ, Xi QY, Sun YP, Wang JL, Zhou JY, Shu G, Jiang QY, Zhang YL. Intestine-specific expression of the β-glucanase in mice. Canadian Journal of Animal Science. Jun. 2014;94(2):287-93. (Year: 2014).*
CN104711253A Abstract Only English Machine Translation; accessed Aug. 10, 2021 at https://worldwide.espacenet.com/patent/search/family/053410971/publication/CN104711253A?q=pn%3DCN104711253A (Year: 2021).*
JP2004180561A Abstract Only English Machine Translation; accessed Aug. 10, 2021 at https://worldwide.espacenet.com/patent/search/family/032752527/publication/JP2004180561A?q=pn%3DJP2004180561A (Year: 2021).*
Bhat, K.S. Genbank direct submission: JX861384.1; submitted Sep. 24, 2012 (Year: 2012).*
Bhat JX861384.1; alignments to instant SEQ ID Nos. 4-10. (Year: 2021).*
16331147-SEQ-IDs-49-50-51-alignments-LOEW-WO-2015142661-A1 (Year: 2021).*
Burnet FM, Immunological aspects of malignant disease, Lancet, Jun. 3, 1967.
Ishida Y., Induced expression of PD-1, a novel member of the immunoglobulin gene superfamily, upon programmed cell death, The EMBO Journal, 1992, vol. 11 No. 11 pp. 3887-3895,.
Li Ying, Advances in PD-1/PD-L1 signaling pathway in tumor immune evasion and its clinical significance, Acad J Chin PLA Med Sch, Jul. 2015, 36 (7).
Andrew M. Intlekofer, At the Bench: Preclinical rationale for CTLA-4 and PD-1 blockade as cancer immunotherapy, Journal of Leukocyte Biology, Jul. 2013, vol. 94.
Ding H., Delivering PD-1 inhibitory signal concomitant with blocking ICOS co-stimulation suppresses lupus-like syndrome in autoimmune BXSB mice, Clinical Immunology, Jan. 4, 2006, 118(2/3), pp. 258-267.
Dong H., Tumor-associated B7-H1 promotes T-cell apoptosis: A potential mechanism of immune evasion, Nature Medicine, Aug. 2002, 8(8), pp. 793-800.
Kisielow M., Isoform-specific knockdown and expression of adaptor protein ShcA using small interfering RNA, Journal of Biochem., 2002, 363, 1-5.
Sharp, RNA Interference-2001, Genes & Dev., 2001, 15:485.
Emily Bernstein, Role for a bidentate ribonuclease in the initiation step of RNA interference, Nature, Jan. 18, 2001, vol. 409.
Antti Nykanen, ATP Requirements and Small Interfering RNA Structure in the RNA Interference Pathway, Cell, Nov. 2, 2001, vol. 107, pp. 309-321.
Sayda M. Elbashir, RNA interference is mediated by 21-and 22-nucleotide RNAs, Genes & Dev., 2001, 15:188.
Porter DL, Chimeric Antigen Receptor—Modified T Cells in Chronic Lymphoid Leukemia, N Engl J Med. Aug. 25, 2011, 365(8): 725-733.
Zhou Xiangju,Tumor personalized precision treatment: clinical application of tumor immune cell therapy and gene sequencing analysis, The 14th National Conference of Tumor Biotherapy Coference Proceedings, May 15, 2015.

* cited by examiner

SEQUENCE LISTING

```
<160> NUMBER OF SEQ ID NOS: 72

<210> SEQ ID NO 1
<211> LENGTH: 861
<212> TYPE: DNA
<213> ORGANISM: Artificial sequence
<220> FEATURE:
<223> OTHER INFORMATION: the sequence is synthetized.

<400> SEQUENCE: 1
atgagtattc aacatttccg tgtcgccctt attccctttt ttgcggcatt ttgccttcct      60
gtttttgctc acccagaaac gctggtgaaa gtaaaagatg ctgaagatca gttgggtgca     120
cgagtgggtt acatcgaact ggatctcaac agcggtaaga tccttgagag ttttcgcccc     180
gaagaacgtt ttccaatgat gagcactttt aaagttctgc tatgtggcgc ggtattatcc     240
cgtattgacg ccgggcaaga gcaactcggt cgccgcatac actattctca gaatgacttg     300
gttgagtact caccagtcac agaaaagcat cttacggatg catgacagt aagagaatta     360 tgcagtgctg ccataaccat gagtgataac actgcggcca acttacttct gacaacgatc     420
ggaggaccga aggagctaac cgcttttttg cacaacatgg ggatcatgt aactcgcctt     480 gatcgttggg aaccggagct gaatgaagcc ataccaaacg acgagcgtga ccacgatg     540 cctgtagcaa tggcaacaac gttgcgcaaa ctattaactg gcgaactact tactctagct     600
tcccggcaac aattaataga ctggatggag gcggataaag ttgcaggacc acttctgcgc     660
tcggcccttc cggctggctg gtttattgct gataaatctg gagccggtga gcgtgggtct     720
cgcggtatca ttgcagcact ggggccagat ggtaagccct cccgtatcgt agttatctac     780
acgacgggga gtcaggcaac tatggatgaa cgaaatagac agatcgctga gataggtgcc     840
tcactgatta agcattggta a                                               861

<210> SEQ ID NO 2
<211> LENGTH: 674
<212> TYPE: DNA
<213> ORGANISM: Artificial sequence
<220> FEATURE:
<223> OTHER INFORMATION: the sequence is synthetized.

<400> SEQUENCE: 2
cccgtagaaa agatcaaagg atcttcttga gatccttttt ttctgcgcgt aatctgctgc      60
ttgcaaacaa aaaaaccacc gctaccagcg gtggtttgtt tgccggatca agagctacca     120
```

```
actcttttc  cgaaggtaac  tggcttcagc  agagcgcaga  taccaaatac  tgtccttcta      180
gtgtagccgt  agttaggcca  ccacttcaag  aactctgtag  caccgcctac  atacctcgct      240
ctgctaatcc  tgttaccagt  ggctgctgcc  agtggcgata  agtcgtgtct  taccggttg       300 gactcaagac  gatagttacc  ggataaggcg  cagcggtcgg  gctgaacggg  gggttcgtgc      360
acacagccca  gcttggagcg  aacgacctac  accgaactga  gatacctaca  gcgtgagcta      420
tgagaaagcg  ccacgcttcc  cgaagggaga  aggcggaca   ggtatccggt  aagcggcagg      480
gtcggaacag  gagagcgcac  gagggagctt  ccaggggaa   acgcctggta  tctttatagt      540
cctgtcgggt  ttcgccacct  ctgacttgag  cgtcgatttt  tgtgatgctc  gtcagggggg      600
cggagcctat  ggaaaaacgc  cagcaacgcg  gccttttac   ggttcctggc  cttttgctgg      660
ccttttgctc  acat                                                            674
```

<210> SEQ ID NO 3  
<211> LENGTH: 147  
<212> TYPE: DNA  
<213> ORGANISM: Artificial sequence  
<220> FEATURE:  
<223> OTHER INFORMATION: the sequence is synthetized.

<400> SEQUENCE: 3

```
atcccgcccc  taactccgcc  cagttccgcc  cattctccgc  cccatggctg  actaattttt      60
tttatttatg  cagaggccga  ggccgcctcg  gcctctgagc  tattccagaa  gtagtgagga     120
ggcttttttg  gaggcctaga  cttttgc                                            147
```

<210> SEQ ID NO 4  
<211> LENGTH: 228  
<212> TYPE: DNA  
<213> ORGANISM: Artificial sequence  
<220> FEATURE:  
<223> OTHER INFORMATION: the sequence is synthetized.

<400> SEQUENCE: 4

```
gtagtcttat  gcaatactct  tgtagtcttg  caacatggta  acgatgagtt  agcaacatgc      60
cttacaagga  gagaaaaagc  accgtgcatg  ccgattggtg  gaagtaaggt  ggtacgatcg     120
tgccttatta  ggaaggcaac  agacgggtct  gacatggatt  ggacgaacca  ctgaattgcc     180
gcattgcaga  gatattgtat  ttaagtgcct  agctcgatac  aataaacg                   228
```

<210> SEQ ID NO 5  
<211> LENGTH: 180  
<212> TYPE: DNA  
<213> ORGANISM: Artificial sequence  
<220> FEATURE:  
<223> OTHER INFORMATION: the sequence is synthetized.

<400> SEQUENCE: 5

```
ggtctctctg  gttagaccag  atctgagcct  gggagctctc  tggctaacta  gggaacccac      60
tgcttaagcc  tcaataaagc  ttgccttgag  tgcttcaagt  agtgtgtgcc  cgtctgttgt     120
gtgactctgg  taactagaga  tccctcagac  ccttttagtc  agtgtggaaa  atctctagca     180
```

<210> SEQ ID NO 6  
<211> LENGTH: 234  
<212> TYPE: DNA  
<213> ORGANISM: Artificial sequence  
<220> FEATURE:  
<223> OTHER INFORMATION: the sequence is synthetized.

<400> SEQUENCE: 6

```
tgctagagat tttccacact gactaaaagg gtctgaggga tctctagtta ccagagtcac    60
acaacagacg ggcacacact acttgaagca ctcaaggcaa gctttattga ggcttaagca   120
gtgggttccc tagttagcca gagagctccc aggctcagat ctggtctaac cagagagacc   180
cagtacaagc aaaaagcaga tcttattttc gttgggagtg aattagccct tcca         234
```

<210> SEQ ID NO 7
<211> LENGTH: 353
<212> TYPE: DNA
<213> ORGANISM: Artificial sequence
<220> FEATURE:
<223> OTHER INFORMATION: the sequence is synthetized.

<400> SEQUENCE: 7

```
atgggtgcga gagcgtcagt attaagcggg ggagaattag atcgcgatgg gaaaaaattc    60
ggttaaggcc aggggggaaag aaaaaatata aattaaaaca tatagtatgg gcaagcaggg   120
agctagaacg attcgcagtt aatcctggcc tgttagaaac atcagaaggc tgtagacaaa   180
tactgggaca gctacaacca tcccttcaga caggatcaga agaacttaga tcattatata   240
atacagtagc aaccctctat tgtgtgcatc aaaggataga gataaaagac accaaggaag   300
ctttagacaa gatagaggaa gagcaaaaca aaagtaagac caccgcacag caa          353
```

<210> SEQ ID NO 8
<211> LENGTH: 233
<212> TYPE: DNA
<213> ORGANISM: Artificial sequence
<220> FEATURE:
<223> OTHER INFORMATION: the sequence is synthetized.

<400> SEQUENCE: 8

```
aggagctttg ttccttgggt tcttgggagc agcaggaagc actatgggcg cagcctcaat    60
gacgctgacg gtacaggcca gacaattatt gtctggtata gtgcagcagc agaacaattt   120
gctgagggct attgaggcgc aacagcatct gttgcaactc acagtctggg gcatcaagca   180
gctccaggca agaatcctgg ctgtggaaag ataccttaaag gatcaacagc tcc          233
```

<210> SEQ ID NO 9
<211> LENGTH: 489
<212> TYPE: DNA
<213> ORGANISM: Artificial sequence
<220> FEATURE:
<223> OTHER INFORMATION: the sequence is synthetized.

<400> SEQUENCE: 9

```
tggggatttg gggttgctct ggaaaactca tttgcaccac tgctgtgcct tggaatgcta    60
gttggagtaa taaatctctg gaacagattg gaatcacacg acctggatgg agtgggacag   120
agaaattaac aattacacaa gcttaataca ctccttaatt gaagaatcgc aaaaccagca   180
agaaaagaat gaacaagaat tattggaatt agataaatgg gcaagtttgt ggaattggtt   240
taacataaca aattggctgt ggtatataaa attattcata atgatagtag gaggcttggt   300
aggtttaaga atagttttg ctgtactttc tatagtgaat agagttaggc agggatattc   360
accattatcg tttcagaccc acctcccaac cccgagggga cccgacaggc ccgaaggaat   420
agaagaagaa ggtggagaga gagacagaga cagatccatt cgattagtga acggatctcg   480
acggttaac                                                            489
```

<210> SEQ ID NO 10

<211> LENGTH: 119
<212> TYPE: DNA
<213> ORGANISM: Artificial sequence
<220> FEATURE:
<223> OTHER INFORMATION: the sequence is synthetized.

<400> SEQUENCE: 10

```
ttttaaaaga aaggggggga ttgggggggta cagtgcaggg gaaagaatag tagacataat      60
agcaacagac atacaaacta aagaattaca aaaacaaatt acaaaaattc aaaattta       119
```

<210> SEQ ID NO 11
<211> LENGTH: 696
<212> TYPE: DNA
<213> ORGANISM: Artificial sequence
<220> FEATURE:
<223> OTHER INFORMATION: the sequence is synthetized.

<400> SEQUENCE: 11

```
atggcccagt ccaagcacgg cctgaccaag gagatgacca tgaagtaccg catggagggc      60
tgcgtggacg gccacaagtt cgtgatcacc ggcgagggca tcggctaccc cttcaagggc     120
aagcaggcca tcaacctgtg cgtggtggag ggcggccccct tgcccttcgc cgaggacatc    180
ttgtccgccc ccttcatgta cggcaaccgc gtgttcaccg agtacccccca ggacatcgtc   240 gactacttca gaactcctg ccccgccggc tacacctggg accgctcctt cctgttcgag     300
gacggcgccg tgtgcatctg caacgccgac atcaccgtga gcgtggagga gaactgcatg    360
taccacgagt ccaagttcta cggcgtgaac ttccccgccg acggccccgt gatgaagaag    420
atgaccgaca ctgggagcc ctcctgcgag aagatcatcc ccgtgcccaa gcagggcatc     480
ttgaagggcg acgtgagcat gtacctgctg ctgaaggacg gtggccgctt gcgctgccag    540
ttcgacaccg tgtacaaggc caagtccgtg ccccgcaaga tgcccgactg cacttcatc     600 cagcacaagc tgacccgcga ggaccgcagc gacgccaaga accagaagtg gcacctgacc   660
gagcacgcca tcgcctccgg ctccgccttg ccctga                              696
```

<210> SEQ ID NO 12
<211> LENGTH: 575
<212> TYPE: DNA
<213> ORGANISM: Artificial sequence
<220> FEATURE:
<223> OTHER INFORMATION: the sequence is synthetized.

<400> SEQUENCE: 12

```
gcccctctcc ctccccccccc cctaacgtta ctggccgaag ccgcttggaa taaggccggt      60
gtgcgtttgt ctatatgtta ttttccacca tattgccgtc ttttggcaat gtgagggccc     120
ggaaacctgg ccctgtcttc ttgacgagca ttcctagggg tctttcccct ctcgccaaag    180
gaatgcaagg tctgttgaat gtcgtgaagg aagcagttcc tctggaagct tcttgaagac    240
aaacaacgtc tgtagcgacc ctttgcaggc agcggaaccc ccacctggc gacaggtgcc     300 tctgcggcca aaagccacgt gtataagata cacctgcaaa ggcggcacaa ccccagtgcc    360
acgttgtgag ttggatagtt gtggaaagag tcaaatggct caccctaagc gtattcaaca    420
aggggctgaa ggatgcccag aaggtacccc attgtatggg atctgatctg gggcctcggt    480
gcacatgctt tacatgtgtt tagtcgaggt taaaaaacgt ctaggccccc cgaaccacgg   540
ggacgtggtt ttcctttgaa aaacacgatg ataat                              575
```

<210> SEQ ID NO 13
<211> LENGTH: 592

<212> TYPE: DNA
<213> ORGANISM: Artificial sequence
<220> FEATURE:
<223> OTHER INFORMATION: the sequence is synthetized.

<400> SEQUENCE: 13

| | | | | | |
|---|---|---|---|---|---|
| aatcaacctc | tggattacaa | aatttgtgaa | agattgactg | gtattcttaa | ctatgttgct | 60 |
| ccttttacgc | tatgtggata | cgctgcttta | atgcctttgt | atcatgctat | tgcttcccgt | 120 |
| atggctttca | ttttctcctc | cttgtataaa | tcctggttgc | tgtctcttta | tgaggagttg | 180 |
| tggcccgttg | tcaggcaacg | tggcgtggtg | tgcactgtgt | tgctgacgc | aaccccact | 240 |
| ggttggggca | ttgccaccac | ctgtcagctc | ctttccggga | ctttcgcttt | ccccctccct | 300 |
| attgccacgg | cggaactcat | cgccgcctgc | cttgcccgct | gctggacagg | ggctcggctg | 360 |
| ttgggcactg | acaattccgt | ggtgttgtcg | gggaaatcat | cgtccttttcc | ttggctgctc | 420 |
| gcctgtgttg | ccacctggat | tctgcgcggg | acgtccttct | gctacgtccc | ttcggccctc | 480 |
| aatccagcgg | accttcctta | ccgcggcctg | ctgccggctc | tgcggcctct | tccgcgtctt | 540 |
| cgccttcgcc | ctcagacgag | tcggatctcc | ctttgggccg | cctccccgcc | tg | 592 |

<210> SEQ ID NO 14
<211> LENGTH: 256
<212> TYPE: DNA
<213> ORGANISM: Artificial sequence
<220> FEATURE:
<223> OTHER INFORMATION: the sequence is synthetized.

<400> SEQUENCE: 14

| | | | | | |
|---|---|---|---|---|---|
| cccctttcacc | gagggcctat | ttcccatgat | tccttcatat | ttgcatatac | gatacaaggc | 60 |
| tgttagagag | ataattggaa | ttaatttgac | tgtaaacaca | aagatattag | tacaaaatac | 120 |
| gtgacgtaga | aagtaataat | ttcttgggta | gtttgcagtt | ttaaaattat | gttttaaaat | 180 |
| ggactatcat | atgcttaccg | taacttgaaa | gtatttcgat | ttcttggctt | tatatatctt | 240 |
| gtggaaagga | cgaaac | | | | | 256 |

<210> SEQ ID NO 15
<211> LENGTH: 1178
<212> TYPE: DNA
<213> ORGANISM: Artificial sequence
<220> FEATURE:
<223> OTHER INFORMATION: the sequence is synthetized.

<400> SEQUENCE: 15

| | | | | | |
|---|---|---|---|---|---|
| gctccggtgc | ccgtcagtgg | gcagagcgca | catcgcccac | agtccccgag | aagttggggg | 60 |
| gaggggtcgg | caattgaacc | ggtgcctaga | gaaggtggcg | cggggtaaac | tgggaaagtg | 120 |
| atgtcgtgta | ctggctccgc | cttttttccg | agggtggggg | agaaccgtat | ataagtgcag | 180 |
| tagtcgccgt | gaacgttctt | tttcgcaacg | ggtttgccgc | cagaacacag | gtaagtgccg | 240 |
| tgtgtggttc | ccgcgggcct | ggcctctttta | cgggttatgg | cccttgcgtg | ccttgaatta | 300 |
| cttccacctg | gctgcagtac | gtgattcttg | atcccgagct | tcgggttgga | agtgggtggg | 360 |
| agagttcgag | gccttgcgct | taaggagccc | cttcgcctcg | tgcttgagtt | gaggcctggc | 420 |
| ctgggcgctg | gggccgccgc | gtgcgaatct | ggtggcacct | tcgcgcctgt | ctcgctgctt | 480 |
| tcgataagtc | tctagccatt | taaaattttt | gatgacctgc | tgcgacgctt | tttttctggc | 540 |
| aagatagtct | tgtaaatgcg | ggccaagatc | tgcacactgg | tatttcggtt | tttggggccg | 600 |
| cgggcggcga | cggggcccgt | gcgtcccagc | gcacatgttc | ggcgaggcgg | ggcctgcgag | 660 |

```
cgcggccacc gagaatcgga cgggggtagt ctcaagctgg ccggcctgct ctggtgcctg    720
gcctcgcgcc gccgtgtatc gccccgccct gggcggcaag gctggcccgg tcggcaccag    780
ttgcgtgagc ggaaagatgg ccgcttcccg gccctgctgc agggagctca aaatggagga    840
cgcggcgctc gggagagcgg gcgggtgagt cacccacaca aaggaaaagg gcctttccgt    900
cctcagccgt cgcttcatgt gactccactg agtaccgggc gccgtccagg cacctcgatt    960
agttctcgag cttttggagt acgtcgtctt taggttgggg ggaggggttt tatgcgatgg    1020
agtttcccca cactgagtgg gtggagactg aagttaggcc agcttggcac ttgatgtaat    1080
tctccttgga atttgccctt tttgagtttg gatcttggtt cattctcaag cctcagacag    1140
tggttcaaag ttttttttctt ccatttcagg tgtcgtga                          1178
```

<210> SEQ ID NO 16
<211> LENGTH: 63
<212> TYPE: DNA
<213> ORGANISM: Artificial sequence
<220> FEATURE:
<223> OTHER INFORMATION: the sequence is synthetized.

<400> SEQUENCE: 16

```
atggccttac cagtgaccgc cttgctcctg ccgctggcct tgctgctcca cgccgccagg     60
ccg                                                                  63
```

<210> SEQ ID NO 17
<211> LENGTH: 324
<212> TYPE: DNA
<213> ORGANISM: Artificial sequence
<220> FEATURE:
<223> OTHER INFORMATION: the sequence is synthetized.

<400> SEQUENCE: 17

```
gacatccaga tgacccagag ccctagctca ctgagcgcca gcgtgggcga cagggtgacc     60
attacctgct ccgccagcca ggacatcagc aactacctga actggtacca gcagaagccc    120
ggcaaggccc ccaagctgct gatctactac acctccaacc tgcactccgg cgtgcccagc    180
aggttcagcg gaagcggcag cggcaccgat ttcaccctga ccatctccag cctgcagccc    240
gaggacttcg ccacctacta ctgccagcag tacaggaagc tcccctggac tttcggccag    300
ggcaccaaac tggagatcaa gcgt                                          324
```

<210> SEQ ID NO 18
<211> LENGTH: 45
<212> TYPE: DNA
<213> ORGANISM: Artificial sequence
<220> FEATURE:
<223> OTHER INFORMATION: the sequence is synthetized.

<400> SEQUENCE: 18

```
ggtggcggtg gctcgggcgg tggtgggtcg ggtggcggcg gatct                     45
```

<210> SEQ ID NO 19
<211> LENGTH: 363
<212> TYPE: DNA
<213> ORGANISM: Artificial sequence
<220> FEATURE:
<223> OTHER INFORMATION: the sequence is synthetized.

<400> SEQUENCE: 19

```
caggtgcagc tggtccagag cggcgccgaa gtgaagaagc ccggcagctc cgtgaaagtg     60
agctgcaagg ccagcggcgg caccttcagc aactactgga tgcactgggt gaggcaggcc    120
```

```
cccggacagg gcctggagtg gatgggcgcc acctacaggg gccacagcga cacctactac    180
aaccagaagt tcaagggccg ggtgaccatc accgccgaca gagcaccag caccgcctac     240 atggaactga gcagcctcag gagcgaggac accgctgtgt attactgcgc caggggcgcc    300
atctacgacg gctacgacgt gctggacaac tggggccagg gcacactagt gaccgtgtcc    360
agc                                                                  363

<210> SEQ ID NO 20
<211> LENGTH: 141
<212> TYPE: DNA
<213> ORGANISM: Artificial sequence
<220> FEATURE:
<223> OTHER INFORMATION: the sequence is synthetized.

<400> SEQUENCE: 20
accacgacgc cagcgccgcg accaccaaca ccggcgccca ccatcgcgtc gcagcccctg     60
tccctgcgcc cagaggcgtg ccggccagcg gcgggggggcg cagtgcacac gaggggggctg   120 gacttcgcct gtgatatcta c                                             141

<210> SEQ ID NO 21
<211> LENGTH: 66
<212> TYPE: DNA
<213> ORGANISM: Artificial sequence
<220> FEATURE:
<223> OTHER INFORMATION: the sequence is synthetized.

<400> SEQUENCE: 21
atctgggcgc ccttggccgg gacttgtggg gtccttctcc tgtcactggt tatcacccctt    60 tactgc                                                               66

<210> SEQ ID NO 22
<211> LENGTH: 126
<212> TYPE: DNA
<213> ORGANISM: Artificial sequence
<220> FEATURE:
<223> OTHER INFORMATION: the sequence is synthetized.

<400> SEQUENCE: 22
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 23
<211> LENGTH: 336
<212> TYPE: DNA
<213> ORGANISM: Artificial sequence
<220> FEATURE:
<223> OTHER INFORMATION: the sequence is synthetized.

<400> SEQUENCE: 23
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatggggggg aaagccgaga aggaagaacc ctcaggaagg cctgtacaat   180
gaactgcaga agataagat ggcggaggcc tacagtgaga ttgggatgaa aggcgagcgc    240 cggagggggca aggggcacga tggcctttac cagggtctca gtacagccac caaggacacc    300
tacgacgccc ttcacatgca ggccctgccc cctcgc                              336
```

<210> SEQ ID NO 24
<211> LENGTH: 123
<212> TYPE: DNA
<213> ORGANISM: Artificial sequence
<220> FEATURE:
<223> OTHER INFORMATION: the sequence is synthetized.

<400> SEQUENCE: 24
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 25
<211> LENGTH: 36
<212> TYPE: DNA
<213> ORGANISM: Artificial sequence
<220> FEATURE:
<223> OTHER INFORMATION: the sequence is synthetized.

<400> SEQUENCE: 25
attcaaaatt ttatcgatgc tccggtgccc gtcagt                              36

<210> SEQ ID NO 26
<211> LENGTH: 22
<212> TYPE: DNA
<213> ORGANISM: Artificial sequence
<220> FEATURE:
<223> OTHER INFORMATION: the sequence is synthetized.

<400> SEQUENCE: 26
tcacgacacc tgaaatggaa ga                                             22

<210> SEQ ID NO 27
<211> LENGTH: 42
<212> TYPE: DNA
<213> ORGANISM: Artificial sequence
<220> FEATURE:
<223> OTHER INFORMATION: the sequence is synthetized.

<400> SEQUENCE: 27
ggtgtcgtga ggatccgcca ccatggcctt accagtgacc gc                       42

<210> SEQ ID NO 28
<211> LENGTH: 31
<212> TYPE: DNA
<213> ORGANISM: Artificial sequence
<220> FEATURE:
<223> OTHER INFORMATION: the sequence is synthetized.

<400> SEQUENCE: 28
gtgtcatctg gatgtccggc ctggcggcgt g                                   31

<210> SEQ ID NO 29
<211> LENGTH: 37
<212> TYPE: DNA
<213> ORGANISM: Artificial sequence
<220> FEATURE:
<223> OTHER INFORMATION: the sequence is synthetized.

<400> SEQUENCE: 29
cacgccgcca ggccggacat ccagatgacc cagagcc                             37

<210> SEQ ID NO 30
<211> LENGTH: 21

```
<212> TYPE: DNA
<213> ORGANISM: Artificial sequence
<220> FEATURE:
<223> OTHER INFORMATION: the sequence is synthetized.

<400> SEQUENCE: 30
acgcttgatc tccagtttgg t                                               21

<210> SEQ ID NO 31
<211> LENGTH: 81
<212> TYPE: DNA
<213> ORGANISM: Artificial sequence
<220> FEATURE:
<223> OTHER INFORMATION: the sequence is synthetized.

<400> SEQUENCE: 31
actggagatc aagcgtggtg gcggtggctc gggcggtggt gggtcgggtg gcggcggatc    60
tcaggtgcag ctggtccaga g                                              81

<210> SEQ ID NO 32
<211> LENGTH: 22
<212> TYPE: DNA
<213> ORGANISM: Artificial sequence
<220> FEATURE:
<223> OTHER INFORMATION: the sequence is synthetized.

<400> SEQUENCE: 32
gctggacacg gtcactagtg tg                                              22

<210> SEQ ID NO 33
<211> LENGTH: 33
<212> TYPE: DNA
<213> ORGANISM: Artificial sequence
<220> FEATURE:
<223> OTHER INFORMATION: the sequence is synthetized.

<400> SEQUENCE: 33
agtgaccgtg tccagcacca cgacgccagc gcc                                  33

<210> SEQ ID NO 34
<211> LENGTH: 23
<212> TYPE: DNA
<213> ORGANISM: Artificial sequence
<220> FEATURE:
<223> OTHER INFORMATION: the sequence is synthetized.

<400> SEQUENCE: 34
gtagatatca caggcgaagt cca                                             23

<210> SEQ ID NO 35
<211> LENGTH: 33
<212> TYPE: DNA
<213> ORGANISM: Artificial sequence
<220> FEATURE:
<223> OTHER INFORMATION: the sequence is synthetized.

<400> SEQUENCE: 35
cgcctgtgat atctacatct gggcgcccTt ggc                                  33

<210> SEQ ID NO 36
<211> LENGTH: 39
<212> TYPE: DNA
<213> ORGANISM: Artificial sequence
<220> FEATURE:
<223> OTHER INFORMATION: the sequence is synthetized.
```

```
<400> SEQUENCE: 36
tctttctgcc ccgtttgcag taaagggtga taaccagtg                          39

<210> SEQ ID NO 37
<211> LENGTH: 21
<212> TYPE: DNA
<213> ORGANISM: Artificial sequence
<220> FEATURE:
<223> OTHER INFORMATION: the sequence is synthetized.

<400> SEQUENCE: 37
aaacggggca gaaagaaact c                                             21

<210> SEQ ID NO 38
<211> LENGTH: 40
<212> TYPE: DNA
<213> ORGANISM: Artificial sequence
<220> FEATURE:
<223> OTHER INFORMATION: the sequence is synthetized.

<400> SEQUENCE: 38
tgctgaactt cactctcagt tcacatcctc cttcttcttc                         40

<210> SEQ ID NO 39
<211> LENGTH: 22
<212> TYPE: DNA
<213> ORGANISM: Artificial sequence
<220> FEATURE:
<223> OTHER INFORMATION: the sequence is synthetized.

<400> SEQUENCE: 39
agagtgaagt tcagcaggag cg                                            22

<210> SEQ ID NO 40
<211> LENGTH: 34
<212> TYPE: DNA
<213> ORGANISM: Artificial sequence
<220> FEATURE:
<223> OTHER INFORMATION: the sequence is synthetized.

<400> SEQUENCE: 40 ggagagggc gtcgacttag cgaggggca gggc                                 34

<210> SEQ ID NO 41
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 41
ccggctaaac tggtaccgca tgagcctcga gtcatgcggt accagtttag cattttttg    59

<210> SEQ ID NO 42
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 42
aattcaaaaa atgctaaact ggtaccgcat gactcgaggc tcatgcggta ccagtttag    59

<210> SEQ ID NO 43
<211> LENGTH: 59
```

```
<212> TYPE: DNA
<213> ORGANISM: Artificial sequence
<220> FEATURE:
<223> OTHER INFORMATION: the sequence is synthetized.

<400> SEQUENCE: 43
ccggcattgt ctttcctagc ggaatctcga gtccgctagg aaagacaatg gttttttg      59

<210> SEQ ID NO 44
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 44
aattcaaaaa aaccattgtc tttcctagcg gactcgagat tccgctagga aagacaatg     59

<210> SEQ ID NO 45
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 45
ccggaggcgc agatcaaaga gagttctcga gctctctttg atctgcgcct tgttttttg     59

<210> SEQ ID NO 46
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 46
aattcaaaaa acaaggcgca gatcaaagag agctcgagaa ctctctttga tctgcgcct    59

<210> SEQ ID NO 47
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 47
ccggccctgt ggttctatta tattactcga gatataatag aaccacaggg aatttttg     59

<210> SEQ ID NO 48
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 48
aattcaaaaa attccctgtg gttctattat atctcgagta atataataga accacaggg    59

<210> SEQ ID NO 49
<211> LENGTH: 58
<212> TYPE: DNA
<213> ORGANISM: Artificial sequence
<220> FEATURE:
<223> OTHER INFORMATION: the sequence is synthetized.

<400> SEQUENCE: 49
```

```
ccggggaacc cattcctgaa attatctcga gaatttcagg aatgggtcca attttttg      58
```

<210> SEQ ID NO 50
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 50

```
aattcaaaaa attggaaccc attcctgaaa ttctcgagat aatttcagga atgggttcc     59
```

<210> SEQ ID NO 51
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 51

```
ccggcaggcc tagagaagtt tcaggctcga gtgaaacttc tctaggcctg cattttttg    59
```

<210> SEQ ID NO 52
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 52

```
aattcaaaaa atgcaggcct agagaagttt cactcgagcc tgaaacttct ctaggcctg     59
```

<210> SEQ ID NO 53
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 53

```
ccggcaggac tcatgtctca atgccctcga gcattgagac atgagtcctg tgttttttg     59
```

<210> SEQ ID NO 54
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 54

```
aattcaaaaa acacaggact catgtctcaa tgctcgaggg cattgagaca tgagtcctg     59
```

<210> SEQ ID NO 55
<211> LENGTH: 55
<212> TYPE: DNA
<213> ORGANISM: Artificial sequence
<220> FEATURE:
<223> OTHER INFORMATION: the sequence is synthetized.

<400> SEQUENCE: 55

```
ccggttctcc gaacgtgtca cgtctcgaga cgtgacacgt tcggagaatt ttttg         55
```

<210> SEQ ID NO 56
<211> LENGTH: 55
<212> TYPE: DNA
<213> ORGANISM: Artificial sequence

```
<220> FEATURE:
<223> OTHER INFORMATION: the sequence is synthetized.

<400> SEQUENCE: 56
aattcaaaaa attctccgaa cgtgtcacgt ctcgagacgt gacacgttcg gagaa        55

<210> SEQ ID NO 57
<211> LENGTH: 19
<212> TYPE: DNA
<213> ORGANISM: Artificial sequence
<220> FEATURE:
<223> OTHER INFORMATION: the sequence is synthetized.

<400> SEQUENCE: 57
tgcagcttct ccaacacat                                                19

<210> SEQ ID NO 58
<211> LENGTH: 18
<212> TYPE: DNA
<213> ORGANISM: Artificial sequence
<220> FEATURE:
<223> OTHER INFORMATION: the sequence is synthetized.

<400> SEQUENCE: 58
cttgtccgtc tggttgct                                                 18

<210> SEQ ID NO 59
<211> LENGTH: 21
<212> TYPE: DNA
<213> ORGANISM: Artificial sequence
<220> FEATURE:
<223> OTHER INFORMATION: the sequence is synthetized.

<400> SEQUENCE: 59
cctttccggg actttcgctt t                                             21

<210> SEQ ID NO 60
<211> LENGTH: 20
<212> TYPE: DNA
<213> ORGANISM: Artificial sequence
<220> FEATURE:
<223> OTHER INFORMATION: the sequence is synthetized.

<400> SEQUENCE: 60
gcagaatcca ggtggcaaca                                               20

<210> SEQ ID NO 61
<211> LENGTH: 21
<212> TYPE: DNA
<213> ORGANISM: Artificial sequence
<220> FEATURE:
<223> OTHER INFORMATION: the sequence is synthetized.

<400> SEQUENCE: 61
catgtacgtt gctatccagg c                                             21

<210> SEQ ID NO 62
<211> LENGTH: 21
<212> TYPE: DNA
<213> ORGANISM: Artificial sequence
<220> FEATURE:
<223> OTHER INFORMATION: the sequence is synthetized.

<400> SEQUENCE: 62
ctccttaatg tcacgcacga t                                             21
```

<210> SEQ ID NO 63
<211> LENGTH: 21
<212> TYPE: DNA
<213> ORGANISM: Artificial sequence
<220> FEATURE:
<223> OTHER INFORMATION: the sequence is synthetized.

<400> SEQUENCE: 63
gacttgtggg gtccttctcc t                                         21

<210> SEQ ID NO 64
<211> LENGTH: 21
<212> TYPE: DNA
<213> ORGANISM: Artificial sequence
<220> FEATURE:
<223> OTHER INFORMATION: the sequence is synthetized.

<400> SEQUENCE: 64
gcagctacag ccatcttcct c                                         21

<210> SEQ ID NO 65
<211> LENGTH: 73
<212> TYPE: DNA
<213> ORGANISM: Artificial Sequence
<220> FEATURE:
<223> OTHER INFORMATION: The sequence is synthesized

<400> SEQUENCE: 65
cgaaactccg gctaaactgg taccgcatga gcctcgagtc atgcggtacc agtttagcat    60
tttttgaatt cgt                                                      73

<210> SEQ ID NO 66
<211> LENGTH: 73
<212> TYPE: DNA
<213> ORGANISM: Artificial Sequence
<220> FEATURE:
<223> OTHER INFORMATION: The sequence is synthesized

<400> SEQUENCE: 66
cgaaactccg gcattgtctt tcctagcgga atctcgagtc cgctaggaaa gacaatggtt    60
tttttgaatt cgt                                                      73

<210> SEQ ID NO 67
<211> LENGTH: 73
<212> TYPE: DNA
<213> ORGANISM: Artificial Sequence
<220> FEATURE:
<223> OTHER INFORMATION: The sequence is synthesized

<400> SEQUENCE: 67
cgaaactccg gaggcgcaga tcaaagagag ttctcgagct ctctttgatc tgcgccttgt    60
tttttgaatt cgt                                                      73

<210> SEQ ID NO 68
<211> LENGTH: 73
<212> TYPE: DNA
<213> ORGANISM: Artificial Sequence
<220> FEATURE:
<223> OTHER INFORMATION: The sequence is synthesized

<400> SEQUENCE: 68
cgaaactccg gccctgtggt tctattatat tactcgagat ataatagaac cacagggaat    60
tttttgaatt cgt                                                      73

```
<210> SEQ ID NO 69
<211> LENGTH: 72
<212> TYPE: DNA
<213> ORGANISM: Artificial Sequence
<220> FEATURE:
<223> OTHER INFORMATION: The sequence is synthesized

<400> SEQUENCE: 69
cgaaactccg gggaacccat tcctgaaatt atctcgagaa tttcaggaat gggtccaatt    60
ttttgaattc gt                                                        72

<210> SEQ ID NO 70
<211> LENGTH: 73
<212> TYPE: DNA
<213> ORGANISM: Artificial Sequence
<220> FEATURE:
<223> OTHER INFORMATION: The sequence is synthesized

<400> SEQUENCE: 70
cgaaactccg gcaggcctag agaagtttca ggctcgagtg aaacttctct aggcctgcat    60
tttttgaatt cgt                                                       73

<210> SEQ ID NO 71
<211> LENGTH: 73
<212> TYPE: DNA
<213> ORGANISM: Artificial Sequence
<220> FEATURE:
<223> OTHER INFORMATION: The sequence is synthesized

<400> SEQUENCE: 71
cgaaactccg gcaggactca tgtctcaatg ccctcgagca ttgagacatg agtcctgtgt    60
tttttgaatt cgt                                                       73

<210> SEQ ID NO 72
<211> LENGTH: 69
<212> TYPE: DNA
<213> ORGANISM: Artificial Sequence
<220> FEATURE:
<223> OTHER INFORMATION: The sequence is synthesized

<400> SEQUENCE: 72
cgaaactccg gttctccgaa cgtgtcacgt ctcgagacgt gacacgttcg gagaattttt    60
tgaattcgt                                                            69
```

SIRNA KNOCKING DOWN HUMAN PD-1 AND RECOMBINANT EXPRESSION CAR-T VECTOR AND THEIR CONSTRUCTION METHODS AND APPLICATIONS

CROSS REFERENCE TO THE RELATED APPLICATIONS

This application is the national phase entry of International Application No. PCT/CN2017/110653, filed on Nov. 13, 2017, which claims priority from the Chinese patent application no. 201611123283.4 filed on Dec. 8, 2016, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBSHHY002_Sequence Listing.txt, created on 08/23/2021 and is 25,454 bytes in size.

TECHNICAL FIELD

This invention belongs to the technical field of tumor immunotherapy, specifically relating to a siRNA knocking down human programmed death receptor 1 (PD-1), recombinant expression CAR-T vector (especially a CAR-T transgene vector eliminating or relieving the immune escape mechanism of tumor by knocking down PD-1) and their construction methods and applications.

BACKGROUND

The theoretical basis of tumor immunotherapy is that the immune system can identify tumor-associated antigens and regulate the body to attack tumor cells (highly specific cytolysis). In the 1950s, Burnet and Thomas made the theory of "immunological surveillance" that holds that mutational tumor cells that often occur in the body can be identified and eliminated by the immune system, laying a theoretical foundation for tumor immunotherapy [Burnet F M. Immunological aspects of malignant disease. Lancet, 1967; 1: 1171-4]. Then, a host of tumor immunotherapies, including cytokine therapy, monoclonal antibody therapy, adoptive immunotherapy and vaccine therapy, have been applied to clinical practice.

In 2013, CAR-T, a more advanced tumor immunotherapy, was successfully put to clinical use, and showed unprecedented clinical effects. CAR-T is short for Chimeric Antigen Receptor T-Cell Immunotherapy. Clinically, the most leading CAR-T is Novartis' CLT019. For patients with refractory-relapsed acute lymphoblastic leukemia and treated with CLT019, the six-month tumor progression-free survival rate can reach 67%, and the longest response time can be more than two years. By cooperating with hospitals, Shanghai Unicar Biomedical Technology Co., Ltd., a Shanghai-based company, treated 36 patients with refractory-relapsed acute lymphoblastic leukemia, among whom 24 as a percentage of 66.6% experienced complete remission. It's a subversive breakthrough in anti-cancer research. CAR-T may be one of the therapies that are the most likely to cure cancer, and was named the best in top 10 breakthroughs of science and technology 2013 by the journal Science.

In spite of the significant effect of CAR-T, there are many difficulties in the treatment of solid tumor, of which an important cause is immunosuppressive checkpoints (see FIG. 1A), which bind to transmit inhibiting signals, inhibit the immunological competence of T cell, play a significant role in immunological tolerance and are also an important reason that causes tumor cells to escape.

PD-1, also known as CD279, is an immuno-inhibitory receptor and a Itype transmembrane protein that belongs to CD28 family. Programmed cell death molecule-1 receptor was got from apoptotic T cell hybridoma through subtractive hybridization and named by Ishida and others in 1992 [Ishida Y, Agata Y, Shibahara K, et al. Induced expression of PD-1, a novel member of the immunoglobulin gene superfamily, upon programmed cell death (J) EMBO J, 1992,11 (11):3887-3895.]. Located on the 2q37.35 chromosome, the human PD-1 gene encodes a transmembrane glycoprotein of around 55 kD. Widely expressed on the surfaces of activated T cells, B cells, mononuclear cells and dendritic cells, PD-1 has 30% of homology with CTLA-4 in structure; there are two tyrosine residues in intracellular region, which are respectively involved in the composition of an immunoreceptor tyrosine-based inhibitory motif (ITIM) of N-terminal and an immunoreceptor tyrosin-based switch motif (ITSM) of C-terminal; composed of an IgV disintegrin-like domain, which can be binding to ligand to inhibit T cell activation, the extracellular region contains more than one glycosylation sites and is highly glycosylated [Li Ying, Jiao Shunchang and others. Role and Clinical Significance of PD-1/PD-L1 Signaling Pathway in Tumor Immune Escape [J]. Acad J Chin PLA Med Sch, J μl 2015,36(7).]

PD-L1 is over-expressed in many cancer tissues, such as NSCLC, melanoma, breast cancer, glioma, lymphoma, leukemia and all kinds of urologic neoplasms, gastrointestinal tumors and genital tumors [Intlekofer A M, Thompson C B. At the bench:preclinical rationale for CTLA-4 and PD-1 blockade as cancer immunotherapy[J]. J Leukoc Biol, 2013, 94(1):25-39.]. In murine and human tumor cells, Parsa found IFN-γ abnormally secreted by T cells, which can induce the high expression of PD-L1 on tumor cells [Ding H, Wu X, Wu J, et al. Delivering PD-1 inhibitory signal concomitant with blocking ICOS co-stimulation suppresses lupus-like syndrome in autoimmune BXSB mice[J]. Clin Immunol, 2006,118(2/3):258-267.]. The high expression of PD-L1 can inhibit the signaling pathways of RAS and PI3K/AKT to regulate the expression of cell cycle checkpoint protein and proteins related to cell proliferation to finally give rise to the inhibition of T cell proliferation [11]. Through Dong and other experiments in vitro and mouse models, it's discovered that activating PD-1/PD-L1 signaling pathway can induce the apoptosis of specific CTL to reduce the sensitivity of CTL to cellular cytotoxicity to cause the immune escape of tumor cells [Dong H, Strome S E, Salomao D R, et al. Tumor-associated B7-H1 promotes T-cell apoptosis: a potential mechanism of immune evasion [J]. Nat Med, 2002,8(8):793-800.].

Clinically, commercialized PD-1 monoclonal antibody is mainly used as immune checkpoint inhibitor to inhibit the immune escape of tumor cells. On Sep. 3, 2014, Bristol-Myers Squibb's anti-PD-1 medicine Opdivo (Nivolumab) was officially launched in Japan, where the medicine is available to patients with melanoma only. The medicine is priced at 72,9849 yen (43,000 yuan) per 100 mg. Now that 2 mg of the medicine needs to be used for each 1 kg of body weight, a person weighing 50 kg needs to use 100 mg of the medicine. Moreover, if the body weight increases by 10 kg, the usage of the medicine needs to be increased by 20 mg (priced at 150,200 yen or 8,778 yuan), and a course of treatment takes about 3 weeks. The price is so expensive that average families can't afford it.

SUMMARY

This invention aims to eliminate the drawbacks of existing technology and provide a siRNA knocking down human PD-1, recombinant expression CAR-T vector and their construction methods and applications.

Purposes of the invention will be achieved with the following technical solutions:

The first purpose of the invention is to provide a siRNA knocking down PD-1, and the said siRNA is selected from any of the following a-g items:

a. nucleotide sequence as shown in SEQ ID NO: 41 and SEQ ID NO: 42;
b. nucleotide sequence as shown in SEQ ID NO: 43 and SEQ ID NO: 44;
c. nucleotide sequence as shown in SEQ ID NO: 45 and SEQ ID NO: 46;
d. nucleotide sequence as shown in SEQ ID NO: 47 and SEQ ID NO: 48;
e. nucleotide sequence as shown in SEQ ID NO: 49 and SEQ ID NO: 50;
f. nucleotide sequence as shown in SEQ ID NO: 51 and SEQ ID NO: 52; and
g. nucleotide sequence as shown in SEQ ID NO: 53 and SEQ ID NO: 54.

Further, a. nucleotide sequence as shown in SEQ ID NO: 41 and SEQ ID NO: 42 is preferable.

The second purpose of the invention is to provide the applications of the said siRNA in the preparation of medicine eliminating or relieving the immune escape mechanism of tumor.

The third purpose of the invention is to provide a recombinant expression vector containing the said siRNA.

Further, the said expression vector is lentiviral expression vector, retroviral expression vector, adenovirus expression vector, adeno-associated virus expression vector or plasmid; lentiviral expression vector containing the said siRNA is preferable.

Further, the said lentiviral expression vector includes the prokaryotic replicon pUC Ori sequence used for plasmid replication, as shown in SEQ ID NO: 2; AmpR sequence with Ampicillin resistance gene and used for the massive proliferation of target strains, as shown in SEQ ID NO: 1; virus-replicon SV40 Ori sequence used for enhancing replication in eukaryote, as shown in SEQ ID NO: 3; lentivirus packaging cis element used for lentivirus packaging; ZsGreen1 green fluorescent protein used for eukaryotic expressing green fluorescence, as shown in SEQ ID NO: 11; IRES ribosome binding sequence used for the common transcription and expression of protein, as shown in SEQ ID NO: 12; human EF1α promoter used for the eukaryotic transcription of chimeric antigen receptor genes, as shown in SEQ ID NO: 15; encoding genes of anti-CD19 chimeric antigen receptors used for making up the second or third generation BCMA integrating identification, transmission and promotion, as shown in SEQ ID NO: 52 or SEQ ID NO: 53; enhanced woodchuck hepatitis virus post-transcriptional regulatory element (eWPRE) used for enhancing transgene expression efficiency, as shown in SEQ ID NO: 13; human RNA polymerase III promoter hU6 used for intracellular transcription of siRNA, as shown in SEQ ID NO: 14.

Further, the second generation lentiviral vectors employed by the said lentivirus packaging cis element include lentivirus 5 terminal LTR, as shown in SEQ ID NO: 5, lentivirus 3 terminal Self-Inactivating LTR, as shown in SEQ ID NO: 6, Gag cis element, as shown in SEQ ID NO: 7, RRE cis element, as shown in SEQ ID NO: 8, env cis element, as shown in SEQ ID NO: 9, and cPPT cis element, as shown in SEQ ID NO: 10.

Further, the third generation lentiviral vectors employed by the said lentivirus packaging cis element include lentivirus 5 terminal LTR, as shown in SEQ ID NO: 5, lentivirus 3 terminal Self-Inactivating LTR, as shown in SEQ ID NO: 6, Gag cis element, as shown in SEQ ID NO: 7, RRE cis element, as shown in SEQ ID NO: 8, env cis element, as shown in SEQ ID NO: 9, cPPT cis element, as shown in SEQ ID NO: 10, and RSV promoter, as shown in SEQ ID NO: 4.

Further, the said eWPRE has 6 enhanced nucleotide mutations, which are g.396G>A, g.397C>T, g.398T>C, g.399G>A, g.400A>T, g.411A>T.

Further, the said anti-BCMA chimeric antigen receptors (the second generation CAR) include serialized CD8 leader chimeric receptor signal peptide, as shown in SEQ ID NO: 16, BCMA single-chain antibody light chain VL, as shown in SEQ ID NO: 17, Optimal Linker C, as shown in SEQ ID NO: 18, BCMA single-chain antibody heavy chain VH, as shown in SEQ ID NO: 19, CD8 chimeric receptor hinge, as shown in SEQ ID NO: 20, CD8 chimeric receptor transmembrane, as shown in SEQ ID NO: 21, CD137 chimeric receptor inducible co-stimulator, as shown in SEQ ID NO: 22, and TCR chimeric receptor T cell activation domain, as shown in SEQ ID NO: 23.

Further, the said anti-BCMA chimeric antigen receptors (the third generation CAR) include serialized CD8 leader chimeric receptor signal peptide, as shown in SEQ ID NO: 16, BCMA single-chain antibody light chain VL, as shown in SEQ ID NO: 17, Optimal Linker C, as shown in SEQ ID NO: 18, BCMA single-chain antibody heavy chain VH, as shown in SEQ ID NO: 19, CD8 chimeric receptor hinge, as shown in SEQ ID NO: 20, CD8 chimeric receptor transmembrane, as shown in SEQ ID NO: 21, CD28 chimeric receptor inducible co-stimulator, as shown in SEQ ID NO: 24, CD137 chimeric receptor inducible co-stimulator, as shown in SEQ ID NO: 22, and TCR chimeric receptor T cell activation domain, as shown in SEQ ID NO: 23.

The fourth purpose of the invention is to provide a construction method for recombinant expression vector containing the said siRNA, which involves the following steps:

(1) Storing in the lentiviral skeleton plasmid pLenti-3G silencer the AmpR sequence with Ampicillin resistance gene (as shown in SEQ ID NO: 1), prokaryotic replicon pUC Ori sequence (as shown in SEQ ID NO: 2), virus-replicon SV40 Ori sequence (as shown in SEQ ID NO: 3), lentivirus packaging cis element used for lentivirus packaging, ZsGreen1 green fluorescent protein (as shown in SEQ ID NO: 11), IRES ribosome binding sequence (as shown in SEQ ID NO: 12), enhanced woodchuck hepatitis virus post-transcriptional regulatory element (eWPRE) (as shown in SEQ ID NO: 13), and human RNA polymerase III promoter hU6 (as shown in SEQ ID NO: 14);

(2) Combining the human EF1α promoter (as shown in SEQ ID NO: 15) and anti-BCMA chimeric antigen receptors used for making up the second or third generation CAR integrating identification, transmission and promotion into, and cloning into lentiviral skeleton plasmid through enzyme digestion, ligation and recombination reactions, the design scheme for the second or third generation CAR, to get the recombinant lentiviral plasmid pCARbcma-silencer designed with the second or third generation CAR;

(3) Respectively cloning into the recombinant lentiviral plasmid got through step (2) the said siRNA and the negative control sequence as shown in SEQ ID NO: 55 and SEQ ID NO: 56 to get PD-1 knock-down recombinant lentiviral plasmids (pCARbcma-1453-pCARbcma-1459 and negative control pCARbcma-1460);

(4) Transfecting recombinant lentiviral plasmids (pCARbcma-1453-pCARbcma-1460) got through step (3) together with lentiviral packaging plasmids pPac-GP and pPac-R as well as membrane protein plasmid pEnv-G, respectively into HEK293T/17 cell, and collecting supernate containing recombinant lentiviral vectors, which will be released into cell culture supernate if packagingd successfully and after gene transcript expression in HEK293T/17 cell; and (5) Respectively getting recombinant lentiviral vectors by purifying recombinant lentivirus supernatant got through step (4) with Ion exchange modes of extraction filtration, adsorption, elution.

Further, in step (1), the second generation lentiviral vectors employed by the said lentivirus packaging cis element, include the lentivirus 5 terminal LTR as shown in SEQ ID NO: 5, lentivirus 3 terminal Self-Inactivating LTR as shown in SEQ ID NO: 6, Gag cis element as shown in SEQ ID NO: 7, RRE cis element as shown in SEQ ID NO: 8, env cis element as shown in SEQ ID NO: 9, and cPPT cis element as shown in SEQ ID NO: 10; the third generation lentiviral vectors employed by the said lentivirus packaging cis element, include the lentivirus 5 terminal LTR as shown in SEQ ID NO: 5, lentivirus 3 terminal Self-Inactivating LTR as shown in SEQ ID NO: 6, Gag cis element as shown in SEQ ID NO: 7, RRE cis element as shown in SEQ ID NO: 8, env cis element as shown in SEQ ID NO. 9, cPPT cis element as shown in SEQ ID NO: 10, and RSV promoter as shown in SEQ ID NO: 4.

Further, in step (2), the said anti-BCMA chimeric antigen receptors used for making up the second generation CAR integrating identification, transmission and promotion, include serialized CD8 leader chimeric receptor signal peptide as shown in SEQ ID NO: 16, BCMA single-chain antibody light chain VL as shown in SEQ ID NO: 17, Optimal Linker C as shown in SEQ ID NO: 18, BCMA single-chain antibody heavy chain VH as shown in SEQ ID NO: 19, CD8 chimeric receptor hinge as shown in SEQ ID NO: 20, CD8 chimeric receptor transmembrane as shown in SEQ ID NO: 21, CD137 chimeric receptor inducible co-stimulator as shown in SEQ ID NO: 22, and TCR chimeric receptor T cell activation domain as shown in SEQ ID NO: 23; the said anti-BCMA chimeric antigen receptors used for making up the third generation CAR integrating identification, transmission and promotion, include serialized CD8 leader chimeric receptor signal peptide as shown in SEQ ID NO: 16, BCMA single-chain antibody light chain VL as shown in SEQ ID NO; 17, Optimal Linker C as shown in SEQ ID NO: 18, BCMA single-chain antibody heavy chain VH as shown in SEQ ID NO: 19, CD8 chimeric receptor hinge as shown in SEQ ID NO: 20, CD8 chimeric receptor transmembrane as shown in SEQ ID NO: 21, CD28 chimeric receptor inducible co-stimulator as shown in SEQ ID NO: 24, CD137 chimeric receptor inducible co-stimulator as shown in SEQ ID NO: 22, and TCR chimeric receptor T cell activation domain as shown in SEQ ID NO: 23.

Further, in step (1), the said eWPRE has 6 enhanced nucleotide mutations, which are g.396G>A, g.397C>T, g.398T>C, g.399G>A, g.400A>T, g.411A>T.

Further, in step (2), the whole CAR gene expression is promoted by human EF1α promoter; located at the N-terminus of CAR coding sequence, CD8 leader chimeric receptor signal peptide is used to direct the localization of CAR protein in cytomembrane; Combined into scfv region, CD19 single-chain antibody light chain VL, Optimal Linker C and CD19 single-chain antibody heavy chain VH are used to identify CD19 antigen; CD8 chimeric receptor hinge is used to anchor scfv in the lateral of cytomembrane; CD8 chimeric receptor transmembrane is used to immobilize the whole chimeric receptor onto cytomembrane; CD137 chimeric receptor inducible co-stimulator is used to stimulate T cell proliferation and cytokine secretion; TCR chimeric receptor T cell activation domain is used to activate the expression of downstream signaling pathway; when scfv region is combined with CD20 antigen, signals are transferred into cells through chimeric receptors to create a series of biological effects including T cell proliferation, increased cytokine secretion, increased anti apoptosis protein, delayed cell death and target cell lysis.

Further, in step (4), the said lentiviral vector has two versions, of which one with fluorescently tagged zsGreen1 is used for in-vitro experiment, while the other without fluorescently tagged zsGreen1 is used for clinical experiment.

Further, in step (5), through the said extraction filtration, the volume of supernatant is controlled at 200 ml-2000 ml, and the vacuum degree of supernatant at −0.5 MPA-0.9 MPA, to prevent loss of vector caused by plugging holes; through the said extraction filtration adsorption, the PH of solution is controlled at 6-8 to prevent inactivation of vector resulting from changes in PH; through the said elution, the ionic strength of eluant is controlled at 0.5M-1.0M to prevent incomplete elution or inactivation of vector arising out of changes in ionic strength.

The fifth purpose of the invention is to provide the applications of the recombinant expression vector containing the said siRNA in the preparation of the medicine eliminating or relieving the immune escape mechanism of tumor in the treatment with CAR-T.

The sixth purpose of the invention is to provide a kind of CART cell, which is the T lymphocyte modified by the said siRNA.

Another purpose of the invention is to provide the applications of the said CAR-T cell in the preparation of medicines for treating multiple myeloma, pancreatic cancer, brain glioma and myeloma.

Such interference effect can last long and remain effective after cell division. And RNAi has very good sequence specificity. [Kisielow, M. et al. (2002) isoform-specific knockdown and expression of adaptor protein ShcA using small interfering RNA, J. of Biochemistry 363: 1-5]. Therefore, RNAi can knock down a type of transcript with its specificity and without affecting other mRNAs with similar sequences. Such features enable siRNA system to show its potential and value in the inhibition of gene expression, gene function research and medicine target validation. In addition, siRNA system can be used to treat relevant diseases, including (1) diseases caused by gene overexpression or misexpression and (2) diseases caused by gene mutation.

The invention is to build the human RNA polymerase III promoter hU6, human EF1α promoter, CD8 leader chimeric receptor signal peptide, BCMA single-chain antibody light chain VL, Optimal Linker C, BCMA single-chain antibody heavy chain VH, CD8 chimeric receptor hinge, CD8 chimeric receptor transmembrane, CD137 chimeric receptor inducible co-stimulator and TCR chimeric receptor T cell activation domain into recombinant lentiviral vector to use the human EF1α promoter to turn on the whole CAR gene expression, localize CAR protein on cell surface, identify BCMA antigen, stimulate T cell proliferation, and activate the expression of downstream signaling pathway; when scfv region is combined with BCMA antigen, to transfer signals into cells through chimeric receptors to create a series of biological effects including T cell proliferation, increased cytokine secretion, increased anti apoptosis protein, delayed cell death and target cell lysis; to turn on the expression of PD1siRNA with the human RNA polymerase III promoter hU6, and via RISC complex, to degrade PD-1 mRNA, inhibit the protein synthesis of PD-1, and interfere with the binding of PD1 to PDL1 to interfere with PD1/PDL1 signaling pathway and inhibit immune escape.

Expression vectors employed by the invention include the prokaryotic replicon pUC Ori used for plasmid replication, pronucleus selection marker AmpR used for the massive proliferation of target strains, virus-replicon SV40 Ori used for enhancing replication in eukaryote, lentivirus packaging cis elements (RSV, 5 terminal LTR, 3 terminal Self-Inactivating LTR, Gag, RRE, env, cPPT) used for lentivirus packaging, human RNA polymerase III promoter hU6 used for intracellular transcription of siRNA, eukaryotic fluorescent labeling protein ZsGreen1 used for eukaryote expressing green fluorescence, co-expression element IRES used for the common transcription and expression of protein, eukaryotic promoter EF1α used for the eukaryotic transcription of chimeric antigen receptor genes, chimeric antigen receptors (CD8 leader, BCMA VL, Optimal Linker C (SEQ ID NO: 19), BCMA VH, CD8 Hinge, CD8 Transmembrane, CD28 (SEQ ID NO: 24), CD137, TCR) used for making up the second and third generations of CAR integrating identification, transmission and promotion, and post-transcriptional regulatory element eWPRE used for enhancing transgene expression efficiency.

The invention involves peptide-containing pharmaceutical preparations, including:

1. Recombinant lentiviral vector skeleton made up of the human RNA polymerase III promoter hU6, AmpR sequence with Ampicillin resistance gene, prokaryotic replicon pUC Ori sequence, virus-replicon SV40 Oni sequence, RSV promoter, human EF1α promoter, lentivirus 5 terminal LTR, lentivirus 3 terminal Self-Inactivating LTR, Gag cis element, RRE cis element, env cis element, cPPT cis element, ribosome binding sequence IRES, ZsGreen1 green fluorescent protein, and woodchuck hepatitis virus post-transcriptional regulatory element (WPRE), which skeleton can carry different therapeutic genes and be widely used in adoptive cell therapy, and carry different siRNAs and be widely used in the treatment of diseases caused by gene overexpression, mixexpression and mutation.

2. Composing recombinant lentiviral vector of recombinant lentiviral vector skeleton, PD1-siRNA, CD8 leader chimeric receptor signal peptide, BCMA single-chain antibody light chain VL, single-chain antibody hinge Linker C, BCMA single-chain antibody heavy chain VH, CD8 chimeric receptor hinge, CD8 chimeric receptor transmembrane, CD28 chimeric receptor inducible co-stimulator, CD137 chimeric receptor inducible co-stimulator and TCR chimeric receptor T cell activation domain, by which recombinant lentiviral vectors got can realize the expression of BCMA chimeric antigen receptors on human T lymphocytes, guide and activate the cytotoxicity of T lymphocyte on BCMA positive cell, and be used to clinically treat multiple myeloma (MM). Expressing the siRNA of programmed death receptor 1 (PD-1) in human T lymphocyte can effectively reduce the expression level of T cell surface programmed death receptor 1, interfere with PD-1/PD-L1 immune negative regulation signaling pathway, and be clinically used to inhibit the immune escape of tumor and improve the curative effect of CAR-T.

The invention employs the siRNA gene silencing technology specific to PD-1. Since 1990s, researchers have discovered that double-stranded RNA ("dsRNA") can be used to inhibit the expression of protein. As such ability of silent gene has great potential in the treatment of human diseases, a great many researchers and commercial entities have invested considerable resources in the development of therapies based on the technology From a mechanism perspective, after entering plant and invertebrate cells, dsRNA is broken down by Type III endonuclease Dicer into siRNA. [Sharp, RNA interference-2001, Genes Dev. 2001, 15:485]. Type III endonuclease Dicer breaks dsRNA down into siRNA with 2 base bulges and 3' sticky ends. [Bernstein, Caudy, Hammond, & Hannon, Role for a bidentate ribonuclease in the initiation step of RNA interference, Nature 2001, 409:363]. In the integration of siRNA with RNA-induced Silencing Complex (RISC), one or more helicase(s) in RISC unwind(s) double-stranded siRNA, making complementary antisense strands direct target recognition. [Nykanen, Haley, & Zamore, ATP requirements and small interfering RNA structure in the RNA interference pathway, Cell 2001, 107:309]. After the integration with corresponding target mRNA, one or more endonuclease(s) in RISC cleave(s) target mRNA, giving rise to mRNA silencing. [Elbashir, Elbashir, Lendeckel, & Tuschl, RNA interference is mediated by 21- and 22-nucleotide RNAs, Genes Dev 2001, 15:188].

PD1siRNA sequence designed by the invention contains 21-bp nucleotide and employs the oligonucleotide pattern of N2[CG]N8[AU]N8[AU]N2. Stem-loop splicing hpRNA is employed between complementary sequences. The success rate of siRNA design has been greatly improved through the screening of siRNA pattern, GC percentage, T or A or G in a row, consecutiver GC, 3'end nt pattern, thermodynamic value, siRNA target, identity, alignment and other conditions.

In the T cell cytotoxicity assay, the system in which the human RNA polymerase III promoter hU6 transcripts PD1siRNA to inhibit the expression of PD-1 employed by the invention, was found to be able to effectively inhibit the transcriptional level of PD-lmRNA upon QPCR test and effectively decrease the expression quantity of T cell surface PD-1 receptor to interfere with PD-1/PDL-1 signaling pathway and inhibit immune escape, and can be clinically used to inhibit the expression level of PD-1 in CAR-T cell and reinforce the cytotoxicity of CAR-T cell on tumor in vivo in the future.

The invention delivers siRNAs by means of lentiviral vectors (see FIG. 2). Firstly, it saves costs and prevents the expensive cost of PD1siRNA synthesis in vitro; secondly, it avoids inefficient delivery of PD1siRNA in vivo; thirdly, it uses the human RNA polymerase III promoter hU6 to express PD1siRNAs, which can effectively utilize intracellular RNA transcription system, highly express corresponding PD1siRNAs and achieve good gene silencing efficacy through a series of enzymatic actions.

The vector skeleton employed by the invention is the third generation lentiviral vector (see FIG. 3A) 3' SIN LTR, from which U3 area is removed, eliminating the possibility of the self-replication of lentiviral vector and greatly increasing security, which includes elements cPPT and WPRE, strengthening the efficiency of transduction and transgene expression, and which employs RSV promoter, ensuring the continuous and efficient transcription of core RNA in lentiviral vector packaging, which employs the human EF1α promoter, so that CAR gene can be continuously expressed in vivo for a long time.

The siRNA knock-down scheme employed by the invention can also be applied to the third generation CAR design scheme. Over the second generation design, the third generation CAR includes CD28 chimeric receptor inducible co-stimulator (SEQ ID NO: 24).

The lentiviral vector column purification system employed by the invention (see FIG. 8) is a lentivirus scale production process developed by the company. The common supercentrifugation or ultracentrifugation method segregates lentiviral particles with the principle of centrifugal sedimentation, which will inevitably leave a lot of impurities of similar sedimentation coefficient and adversely affect follow-up experiments. Also, the complex tubing process, cumbersome operations and multiple container transformations will increase the risk of contamination. However, the lentiviral vector column purification process employed by the invention is semi-automatic and entirely done in one-hundred-grade experimental region, avoiding cumbersome manual operations and risk of contamination and retrieving lentiviral vectors completely meeting clinical standards in endotoxin, mycoplasma and other indicators. The development of fully automatic purifier may be followed up.

The CAR design scheme employed by the invention can also be applied to the structure of the second generation lentiviral vector. The major difference in structure between the second and third generation lentiviral vectors (see FIG. 3B) is that the third generation lentiviral vector replaces the U3 area of the second vector 5'LTR with RSV promoter to eliminate dependency on Tat protein in U3 transcription to remove Tat sequence from the structural gene of lentivirus and improve the transcriptional level and continuity of lentiviral genome. The second generation lentiviral vector is mainly different from the third one in the transcriptional method of genome, and thus the CAR design scheme employed by the invention can be applied to the two generations of lentiviral vectors.

The third generation lentiviral skeleton plasmid involved in the invention employs enhanced WPRE, which, compared to the WPRE employed by Carl H. June and others at the University of Pennsylvania (Porter D L, Levine B L, Kalos M, Bagg A, June C H. Chimeric antigen receptor modified T cells in chronic lymphoid leukemia. N Engl J Med 2011; 365:725-33.), has 6 enhanced nucleotide mutations (g.396G>A, g.397C>T, g.398T>C, g.399G>A, g.400A>T, g.411A>T), and can strengthen the polyadenylation of primary transcripts, intracellular content of mRNA and transgenic expression efficiency.

The Lentival packaging system involved in the invention is a four-plasmid packaging system without helper virus, which produces recombinant lentiviral vectors by transfecting four plasmids into HEK293T/17 cells. Recombined lentiviral vector is a replication-defective vector that can integrate foreign fragments into host gene, is disposable and can't be replicated or proliferated, thereby greatly increasing security.

The lentiviral vector employed by the invention has two versions, of which one with fluorescently tagged zsGreen1 is used for in-vitro experiment, while the other without fluorescently tagged zsGreen1 is used for clinical experiment.

The Linker design for scfv employed by the invention can significantly improve cytokine secretion, as well as the cytotoxicity in vitro and clinical treatment effect of CAR-T cell.

It can be seen that recombinant lentiviral vectors said in the invention can give reliable transgenic guarantee for the CAR-T treatment of multiple myeloma (MM), and also interfere with the immune escape mechanism of tumor, improve the curative effect of CAR-T, and greatly reduce the medical expense of patients.

The PD-1 knock-down siRNA expression cassette and its siRNA expression products described in the invention can be used not only in CAR19-T treatment of multiple myeloma (MM) to eliminate or alleviate the immune escape mechanism of tumor, but also to inhibit immune escape mechanisms in the treatment of pancreatic cancer, brain glioma, bone cancer and other kinds of tumors with CAR-T.

BRIEF DESCRIPTION OF THE DRAWINGS

FIG. 7A shows the sequencing alignment result of pCARbcma-1453, the top line shows SEQ ID NO: 41, the bottom line shows SEQ ID NO: 65.

FIG. 7B shows the sequencing alignment result of pCARbcma-1454, the top line shows SEQ ID NO: 43, the bottom line shows SEQ ID NO: 66;

FIG. 7C shows the sequencing alignment result of pCARbcma-1455, the top line shows SEQ ID NO: 45, the bottom line shows SEQ ID NO: 67;

FIG. 7D shows the sequencing alignment result of pCAR-bcma-1456, the top line shows SEQ ID NO: 47, the bottom line shows SEQ ID NO: 68;

FIG. 7E shows the sequencing alignment result of pCAR-bcma-1457, the top line shows SEQ ID NO: 49, the bottom line shows SEQ ID NO: 69;

FIG. 7F shows the sequencing alignment result of pCAR-bcma-1458, the top line shows SEQ ID NO: 51, the bottom line shows SEQ ID NO: 70;

FIG. 7G shows the sequencing alignment result of pCAR-bcma-1459, the top line shows SEQ ID NO: 53, the bottom line shows SEQ ID NO: 71;

FIG. 7H shows the sequencing alignment result of pCAR-bcma-1460, the top line shows SEQ ID NO: 55, the bottom line shows SEQ ID NO: 72;

FIGS. 12A and 12B show a WB detection chart of CAR protein expression. FIG. 12 B are the beta-actin bands;

DETAILED DESCRIPTION OF THE EMBODIMENTS

Figure 1:
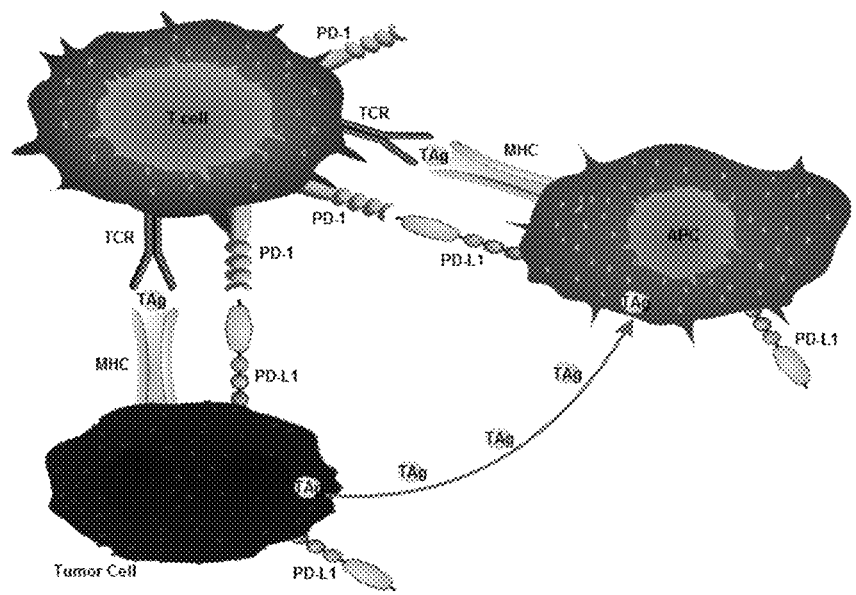
FIG. 1 is a schematic diagram of PD-1/PD-L1 signaling pathway described in the invention.
Figure 2:
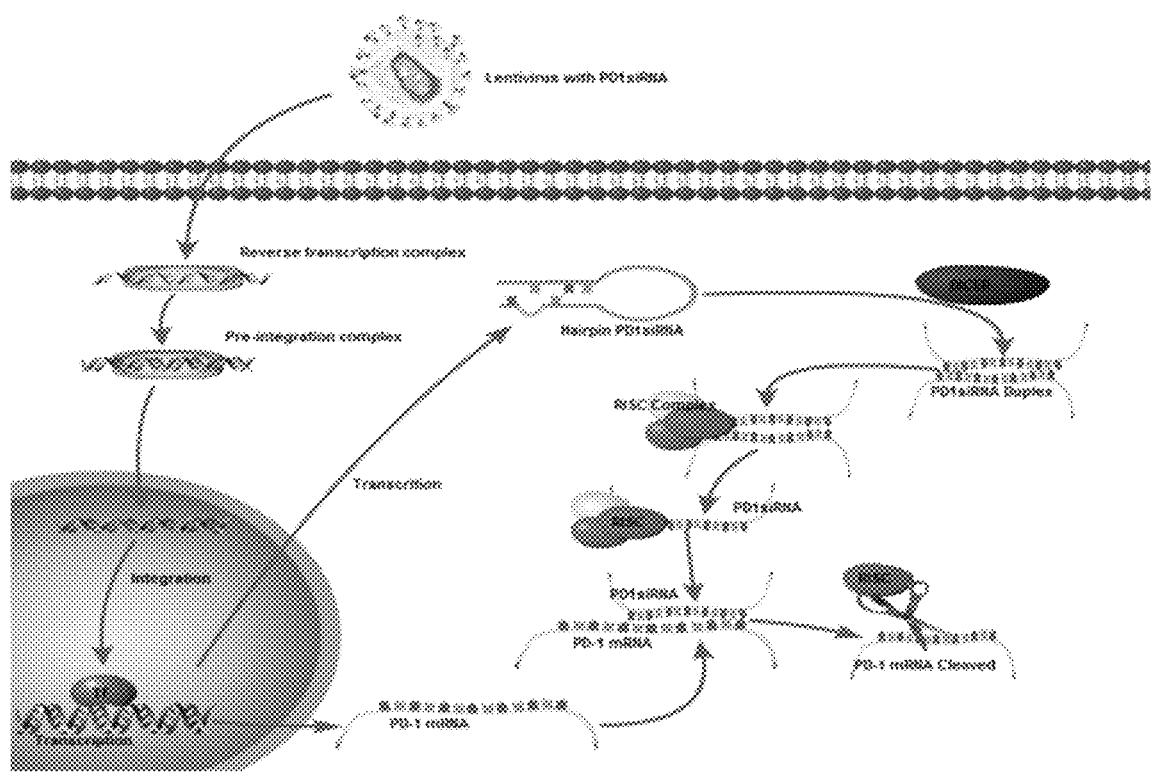
FIG. 2 is a schematic diagram of PD1siRNA delivery by lentivirus described in the invention.
Figure 3:
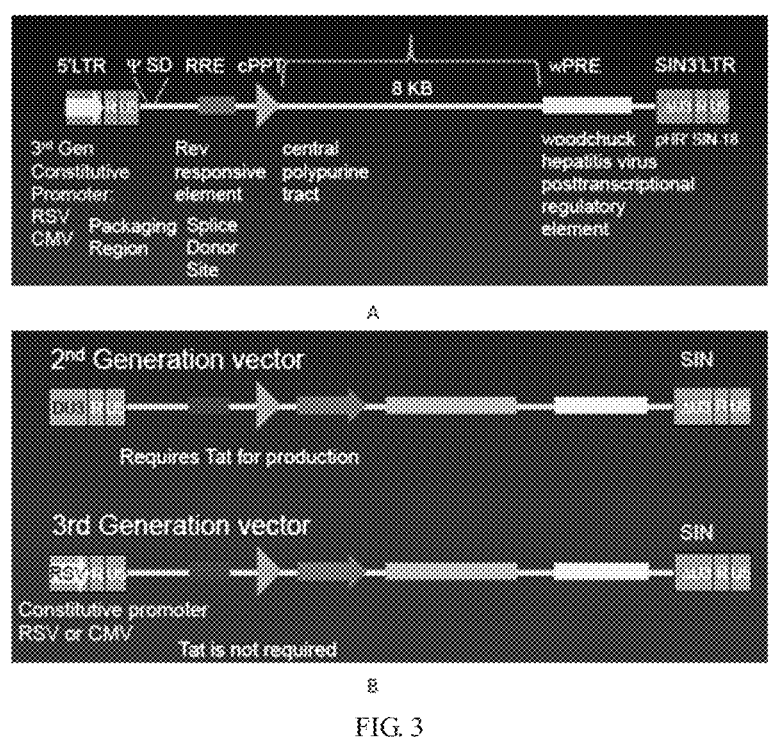
FIG. 3A is a structure diagram of the $3^{rd}$ generation lentiviral vector adopted by the invention.
FIG. 3B is a comparison between the $2^{nd}$ generation and $3^{rd}$ generation lentiviral vector structure.

The following embodiments are only to illustrate the invention not to limit its scope. An experimental method without specific conditions stated in an embodiment is generally in accordance with conventional conditions or conditions recommended by the manufacturer.

Embodiment 1 To Construct Recombinant Lentiviral Vector

I. Material

1. Lentiviral cytoskeleton plasmid pLenti-3G silencer, lentiviral packaging plasmid pPac-GP, pPac-R and membrane protein plasmid pEnv-G, HEK293T/17 cells, homologous recombinase, Oligo Annealing Buffer were provided by Shiao (Shanghai) Biotech Co., Ltd.;

2. Primers: Primers required for amplification of DNA fragments and target sites and designed in the principle of primer design were synthesized by a Shanghai-based company, including:

EF1α-F:
(SEQ ID NO: 25)
5'-ATTCAAAATTTTATCGATGCTCCGGTGCCCGTCAGT-3'

EF1α-R:
(SEQ ID NO: 26)
5'-TCACGACACCTGAAATGGAAGA-3'

CD8 leader-F:
(SEQ ID NO: 27)
5'-GGTGTCGTGAGGATCCGCCACCATGGCCTTACCAGTGACCGC-3'

CD8 leader-R:
(SEQ ID NO: 28)
5'-GTGTCATCTGGATGTCCGGCCTGGCGGCGTG-3'

VL-F:
(SEQ ID NO: 29)
5'-CACGCCGCCAGGCCGGACATCCAGATGACCCAGAGCC-3'

VL-R:
(SEQ ID NO: 30)
5'-ACGCTTGATCTCCAGTTTGGT-3'

OLC-VH-F:
(SEQ ID NO: 31)
5'-ACTGGAGATCAAGCGTGGTGGCGGTGGCTCGGGCGGTGGTGGGTCG
GGTGGCGGCGGATCTCAGGTGCAGCTGGTCCAGAG-3'

VH-R:
(SEQ ID NO: 32)
5'-GCTGGACACGGTCACTAGTGTG-3'

CD8 Hinge-F:
(SEQ ID NO: 33)
5'-AGTGACCGTGTCCAGCACCACGACGCCAGCGCC-3'

CD8 Hinge-R:
(SEQ ID NO: 34)
5'-GTAGATATCACAGGCGAAGTCCA-3'

CD8 Transmembrane-F:
(SEQ ID NO: 35)
5'-CGCCTGTGATATCTACATCTGGGCGCCCTTGGC-3'

CD8 Transmembrane-R:
(SEQ ID NO: 36)
5'-TCTTTCTGCCCCGTTTGCAGTAAAGGGTGATAACCAGTG-3'

CD137-F:
(SEQ ID NO: 37)
5'-AAACGGGGCAGAAAGAAACTC-3'

CD137-R:
(SEQ ID NO: 38)
5'-TGCTGAACTTCACTCTCAGTTCACATCCTCCTTCTTCTTC-3'

TCR-F:
(SEQ ID NO: 39)
5'-AGAGTGAAGTTCAGCAGGAGCG-3'

TCR-R:
(SEQ ID NO: 40)
5'-GGAGAGGGGCGTCGACTTAGCGAGGGGGCAGGGC-3' siRNA1453-F:
(SEQ ID NO: 41)
5'-CCGGCTAAACTGGTACCGCATGAGCCTCGAGTCATGCGGTACCAGT
TTAGCATTTTTTG-3' siRNA1453-R:
(SEQ ID NO: 42)
5'-AATTCAAAAAATGCTAAACTGGTACCGCATGACTCGAGGCTCATGC
GGTACCAGTTTAG-3'

-continued siRNA1454-F:
(SEQ ID NO: 43)
5'-CCGGCATTGTCTTTCCTAGCGGAATCTCGAGTCCGCTAGGAAAGAC
AATGGTTTTTTG-3' siRNA1454-R:
(SEQ ID NO: 44)
5'-AATTCAAAAAAACCATTGTCTTTCCTAGCGGACTCGAGATTCCGCT
AGGAAAGACAATG-3' siRNA1455-F:
(SEQ ID NO: 45)
5'-CCGGAGGCGCAGATCAAAGAGAGTTCTCGAGCTCTCTTTGATCTGC
GCCTTGTTTTTTG-3' siRNA1455-R:
(SEQ ID NO: 46)
5'-AATTCAAAAAACAAGGCGCAGATCAAAGAGAGCTCGAGAACTCTC
TTTGATCTGCGCCT-3' siRNA1456-F:
(SEQ ID NO: 47)
5'-CCGGCCCTGTGGTTCTATTATATTACTCGAGATATAATAGAACCAC
AGGGAATTTTTG-3' siRNA1456-R:
(SEQ ID NO: 48)
5'-AATTCAAAAAATTCCCTGTGGTTCTATTATATCTCGAGTAATATAA
TAGAACCACAGGG-3' siRNA1457-F:
(SEQ ID NO: 49)
5'-CCGGGGAACCCATTCCTGAAATTATCTCGAGAATTTCAGGAATGGG
TCCAATTTTTG-3' siRNA1457-R:
(SEQ ID NO: 50)
5'-AATTCAAAAAATTGGAACCCATTCCTGAAATTCTCGAGATAATTTCA
GGAATGGGTCC-3' siRNA1458-F:
(SEQ ID NO: 51)
5'-CCGGCAGGCCTAGAGAAGTTTCAGGCTCGAGTGAAACTTCTCTAGG
CCTGCATTTTTG-3' siRNA1458-R:
(SEQ ID NO: 52)
5'-AATTCAAAAAATGCAGGCCTAGAGAAGTTTCACTCGAGCCTGAAA
CTTCTCTAGGCCTG-3' siRNA1459-F:
(SEQ ID NO: 53)
5'-CCGGCAGGACTCATGTCTCAATGCCCTCGAGCATTGAGACATGAGT
CCTGTGTTTTTG-3' siRNA1459-R:
(SEQ ID NO: 54)
5'-AATTCAAAAAACACAGGACTCATGTCTCAATGCTCGAGGGCATTGA
GACATGAGTCCTG-3' siRNA1460-F:
(SEQ ID NO: 55)
5'-CCGGTTCTCCGAACGTGTCACGTCTCGAGACGTGACACGTTCGGAG
AATTTTTTG-3' siRNA1460-R:
(SEQ ID NO: 56)
5'-AATTCAAAAAATTCTCCGAACGTGTCACGTCTCGAGACGTGACACG
TTCGGAGAA-3'

PD-1-QPCR-F:
(SEQ ID NO: 57)
5'-TGCAGCTTCTCCAACACAT-3'

PD-1-QPCR-R:
(SEQ ID NO: 58)
5'-CTTGTCCGTCTGGTTGCT-3'

WPRE-QPCR-F:
(SEQ ID NO: 59)
5'-CCTTTCCGGGACTTTCGCTTT-3'

-continued

WPRE-QPCR-R:
(SEQ ID NO: 60)
5'-GCAGAATCCAGGTGGCAACA-3'

Actin-QPCR-F:
(SEQ ID NO: 61)
5'-CATGTACGTTGCTATCCAGGC-3'

Actin-QPCR-R:
(SEQ ID NO: 62)
5'-CTCCTTAATGTCACGCACGAT-3'

CAR-QPCR-F:
(SEQ ID NO: 63)
5'-GACTTGTGGGGTCCTTCTCCT-3'

CAR-QPCR-R:
(SEQ ID NO: 64)
5'-GCAGCTACAGCCATCTTCCTC-3'

3. The DNA sequences shown in SEQ ID NO: 15-SEQ ID NO: 64 were synthesized by Shanghai Generay Biotech Co., Ltd., and stored as oligonucleotide dry powder or plasmid;

4. Tool enzymes BspE I, EcoR I, BamH I, Pvu I, Cla I and T4 DNA ligases were purchased from NEB;

5. PrimerSTAR HS DNA Polymerase, RN were purchased from Takara;

6. 0.22 μm-0.8 μm PES filters were purchased from millipore;

7. The Plasmid Extraction Kit and Agarose Gel Recovery Kit were purchased from MN;

8. TOP 10 Competent Cell were purchased from tiangen;

9. NaCl, KCl, $Na_2HPO_4 \cdot 12H_2O$, $KH_2PO_4$, Trypsin, EDTA, $CaCl_2$, NaOH, PEG6000 were purchased from Shanghai Sangon Biotech;

10. Opti-MEM, FBS, DMEM, 1640, Pen-Srep, Hepes were purchased from invitrogen;

11. Biotinylated protein L was purchased from GeneScript;

12. HRP-labeled secondary antibodies and DAB working fluid were purchased from ZSGB-BIO;

13. ECL+plus™ Western blotting system was purchased from Amersham;

14. DNeasy kit was purchased from Shanghai Generay Biotech Co., Ltd.;

15. Lymphocyte Separation Medium were purchased from Dakewe Biotech Co., Ltd.;

16. SA-HRP were purchased from Yeasen Biotech Co., Ltd.;

17. Mycoplasma Detection Kit, Endotoxin Detection Kit and BCMA-K562 Cell and BCMA-PDL1-K562 cell strains were purchased from Shiao (Shanghai) Biotech Co., Ltd.;

18. LDH Detection Kit were purchased from promega;

II. Construction Method of Recombinant Lentiviral Vectors lvCARbcma-1453-lvCARbcma-1460

Figure 4:
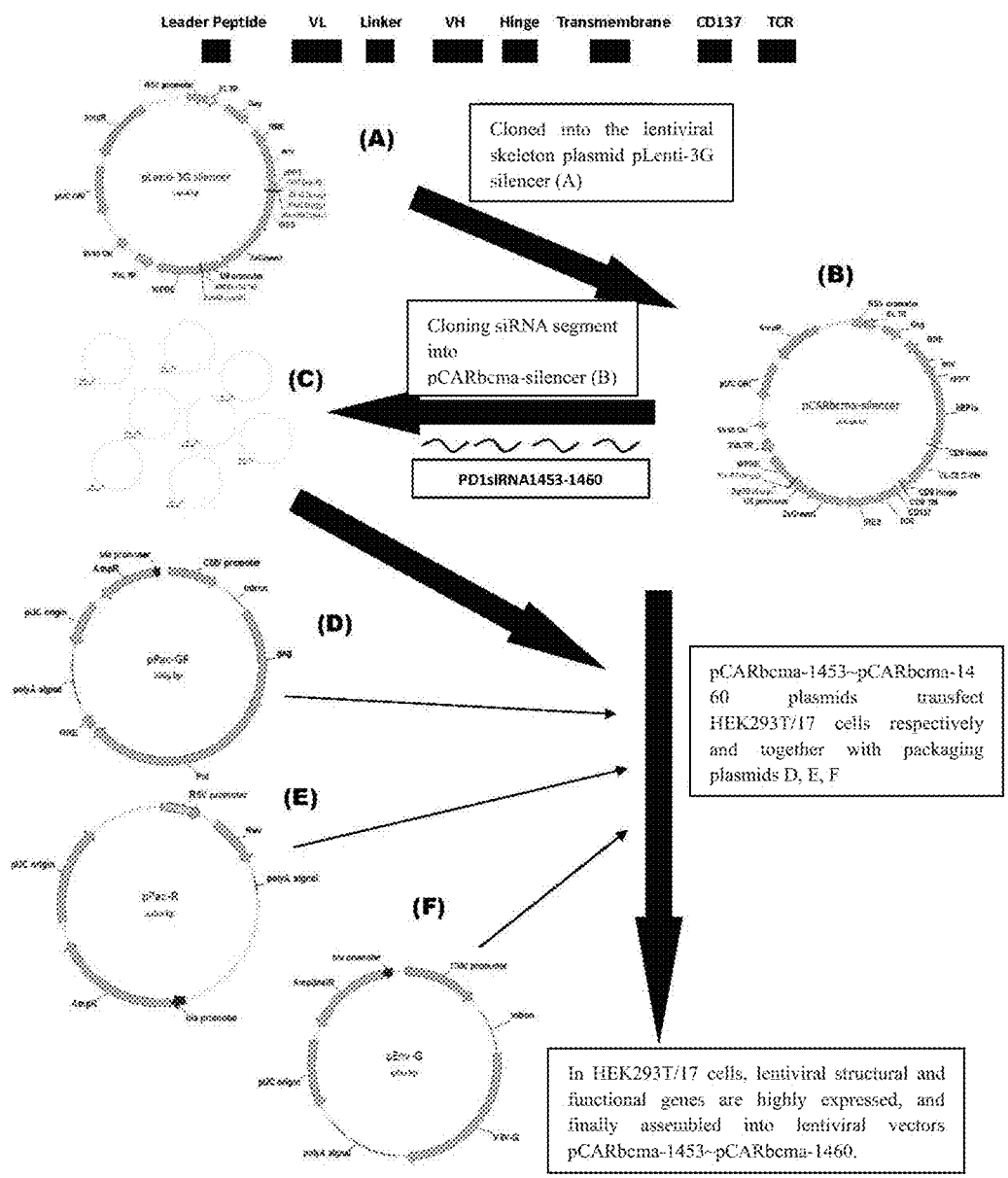
FIG. 4 is a flowchart of the construction of the recombinant lentiviral vector described in the invention; Among them, (A) is a structure diagram of lentiviral cytoskeleton plasmid pLenti-3G silencer; (B) is a structure diagram of pCARbcma-silencer plasmid; (C) is a schematic diagram of pCARbcma-1453-pCARbcma-1460 plasmid; (D) is a structure diagram of lentiviral packaging plasmid pPac-GP; (E) is a structure diagram of lentiviral packaging plasmid pPac-R; (F) is a structure diagram of membrane protein pEnv-G.

See FIG. 4. The construction method of the recombinant lentiviral vector described in the invention is as follows:

1. The human EF1α promoters, CD8 leader chimeric receptor signal peptide, BCMA single chain antibody light chain VL, Optimal Linker C, BCMA single chain antibody heavy chain VH, CD8 chimeric receptor hinge, CD8 transmembrane transmembrane domain chimeric receptor, the chimeric receptor co-stimulation factor—CD137, TCR and T cell activation domain chimeric receptor fragments were cloned into the lentiviral cytoskeleton plasmid pLenti-3G silencer to obtain recombinant lentiviral plasmid pCARbcma-silencer, and the siRNA fragments were connected into pCARbcma-silencer respectively to obtain IL-6 knockdown recombinant lentiviral plasmids pCARbcma-1453-pCARbcma-1460.

Figure 5:
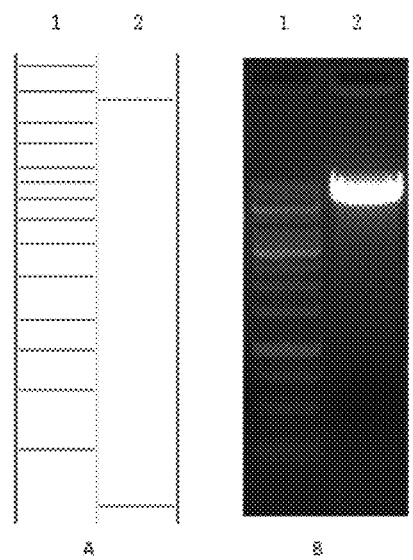
FIG. 5A is the schematic diagram of the restriction enzyme digestion prediction of lentiviral cytoskeleton plasmid pLenti-3G silencer; of which lane 1 is 1 kb DNA ladder Marker: the bands from top to bottom are: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; lane 2 is the Cla I+BamH I digestion prediction of pLenti-3G silencer: the bands from top to bottom are: 7381 bp, 23 bp.
FIG. 5B is the enzymatic cleavage agarose gel electrophoregram of lentiviral cytoskeleton plasmid pLenti-3G silencer, and lane1 is the electrophoretic result of 1 kb DNA ladder Marker; lane2 is the enzyme-digested electrophoretic result of Cla I+BamH I.

(1) The lentiviral cytoskeleton plasmid pLenti-3G silencer was double digested with Cla I and BamH I restriction enzymes. The product was electrophoresed on a 1.5% agarose gel to confirm the 7381 bp fragment V1 (see FIG. 5), then such gel was recovered and placed in an Eppendorf tube. The corresponding fragments were recovered with Agarose Gel Recovery Kit of MN (see Table 1), and the purity and concentration of the product were determined;

TABLE 1

| Procedures for the recovery of agarose gels | |
| --- | --- |
| 1. Sol | Add the sol solution in a ratio of 200 µl NTI/100 mg gel, and place it in a 50° C. water bath for 5-10 minutes. |
| 7. Bind to DNA | Centrifuge at 11,000 g for 30 seconds, and discard the filtrate. |
| 8. Wash membrane | Add 700 µl NT3, centrifuge at 11,000 g for 30 seconds, and discard the filtrate |
| 9. Wash membrane | Repeat the third step once |
| 10. Dry | Centrifuge at 11,000 g for 1 minute, replace with a new collection tube, and leave it at room temperature for 1 minute. |
| 11. Elute DNA | Add 15-30 µl NE, leave it at room temperature for 1 minute, centrifuge at 11,000 g for 1 minute, and then collect the filtrate. |

(2) Use the primers EF1α-F and EF1α-R with the synthesized SEQ ID NO: 15 as a template, and apply the system in Table 2. PCR circulation condition was: 98° C. 3 min, (98° C. 10 sec, 55° C. 15 sec, 72° C. 2 min)*35 cycle, 72° C. 10 min. The product was electrophoresed on a 1.5% agarose gel to confirm the 1208 bp fragment a, then such gel was recovered and placed in an Eppendorf tube. The corresponding fragments were recovered with Agarose Gel Recovery Kit of MN (see Table 1), and the purity and concentration of the product were determined-,

TABLE 2

| 50 µl PCR reaction system | |
| --- | --- |
| Reagent | Volume (µl) |
| H$_2$O | 32.5 |
| 5 × Buffer (with Mg2+) | 10 |
| dNTP (2.5 mM each) | 4 |
| Primer1 (+)(10 µM) | 1 |
| Primer2 (−)(10 µM) | 1 |
| Template | 1 |
| PrimeSTAR | 0.5 |

(3) Use the primers CD8 leader-F and CD8 leader-R with the synthesized SEQ ID NO: 16 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 101 bp fragment b, then such gel was recovered and placed in an Eppendorf tube. The corresponding fragments were recovered with Agarose Gel Recovery Kit of MN (see Table 1), and the purity and concentration of the product were determined;

(4) Use the primers VL-F and VL-R with the synthesized SEQ ID NO: 17 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 336 bp fragment c, then such gel was recovered and placed in an Eppendorf tube. The corresponding fragments were recovered with Agarose Gel Recovery Kit of MN (see Table 1), and the purity and concentration of the product were determined;

(5) Use the primers OLC-VH-F and VH-R with the synthesized SEQ ID NO: 19 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 421 bp fragment d, then such gel was recovered and placed in an Eppendorf tube. The corresponding fragments were recovered with Agarose Gel Recovery Kit of MN (see Table 1), and the purity and concentration of the product were determined;

(6) Use the primers CD8 Hinge-F and CD8 Hinge-R with the synthesized SEQ ID NO: 20 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 147 bp fragment e, then such gel was recovered and placed in an Eppendorf tube. The corresponding fragments were recovered with Agarose Gel Recovery Kit of MN (see Table 1), and the purity and concentration of the product were determined;

(7) Use the primers CD8 Transmembrane-F and CD8 Transmembrane-R with the synthesized SEQ ID NO: 21 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 100 bp fragment f, then such gel was recovered and placed in an Eppendorf tube. The corresponding fragments were recovered with Agarose Gel Recovery Kit of MN (see Table 1), and the purity and concentration of the product were determined;

(8) Use the primers CD137-F and CD137-R with the synthesized SEQ ID NO: 22 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 142 bp fragment g, then such gel was recovered and placed in an Eppendorf tube. The corresponding fragments were recovered with Agarose Gel Recovery Kit of MN (see Table 1), and the purity and concentration of the product were determined;

(9) Use the primers TCR-F and TCR-R with the synthesized SEQ ID NO: 23 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 335 bp fragment h, then such gel was recovered and placed in an Eppendorf tube. The corresponding fragments were recovered with Agarose Gel Recovery Kit of MN (see Table 1), and the purity and concentration of the product were determined;

(10) Applying the system in Table 3, 1 µl each of DNA fragments b, c and d were taken as templates to add to Eppendorf tubes except for primers. PCR circulation condition was: 98° C. 3 min, (98° C. 10 sec, 60° C. 10 sec, 72° C. 40 sec)*6 cycle. To add primer CD8 leader-F/VH-R with the conditions as (98° C. 10 sec, 60° C. 10 sec, 72° C. 40 sec)*24 cycle, 72° C. 5 min. The product was electrophoresed on a 1.5% agarose gel to confirm the 814 bp fragment i, then such gel was recovered and placed in an Eppendorf tube. The corresponding fragments were recovered with Agarose Gel Recovery Kit of MN (see Table 1), and the purity and concentration of the product were determined;

TABLE 3

50 μl overlapping PCR reaction system

| Reagent | Volume (μl) |
| --- | --- |
| H₂O | 33.5-1* number of templates |
| 5 × Buffer (with Mg2+) | 10 |
| dNTP (2.5 mM each) | 4 |
| Primer1 (+) (10 μM) | 1 |
| Primer2 (−) (10 μM) | 1 |
| Template | 1* number of templates |
| PrimeSTAR | 0.5 |

(11) Applying the system in Table 3, 1 μl each of DNA fragments e, f, g and h were taken as templates to add to Eppendorf tubes except for primers. PCR circulation condition was: 98° C. 3 min, (98° C. 10 sec, 60° C. 10 sec, 72° C. 40 sec)*6 cycle. To add primer CD8 Hinge-F/TCR-R with the conditions as (98° C. 10 sec, 60° C. 10 sec, 72° C. 40 sec)*24 cycle, 72° C. 5 min. The product was electrophoresed on a 1.5% agarose gel to confirm the 704 bp fragment j, then such gel was recovered and placed in an Eppendorf tube. The corresponding fragments were recovered with Agarose Gel Recovery Kit of MN (see Table 1), and the purity and concentration of the product were determined;

(12) The DNA fragments V1, a, i, j were added to the Eppendorf tubes in a total volume of 5 μl with a molar ratio of 1:1:1:1. 15 μl of the homologous recombinase reaction solution was added to the tubes, and the mixtures were incubated at 42° C. for 30 minutes. Place them on ice for 2-3 minutes. Add the reaction solution to 50 μl of TOP10, gently rotate to mix the contents, place them on ice for 30 minutes, then put the tubes in the thermostatic water bath pre-warmed to 42° C. for 90 seconds, and quickly transfer the tubes in an ice bath. The cells were allowed to cool for 2-3 minutes. Add 900 μl of LB medium to each tube, then put the tubes to a 37° C. shaker and incubate for 1 hour to resuscitate the bacteria. Take 100 μl of transformant bacteria solution to apply to an Amp LB agar plate, invert the plate, and culture in a thermostatic incubator at 37° C. for 16 hours.

Figure 6:
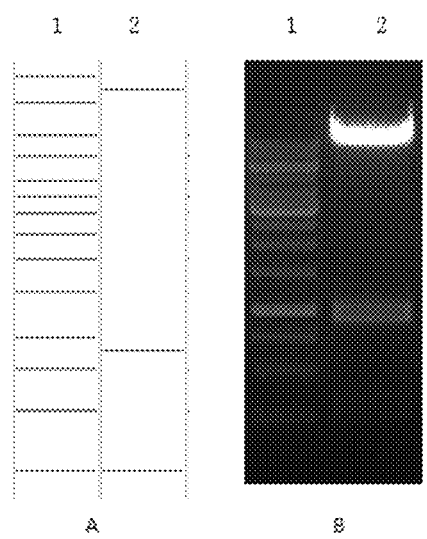
FIG. 6A is the schematic diagram of the restriction enzyme digestion prediction of recombinant lentiviral plasmid pCARbcma-silencer, of which lane 1 is 1 kb DNA ladder Marker: the bands from top to bottom are: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; lane 2 is the Pvu I digestion prediction of pCARbcma-silencer: the bands from top to bottom are: 8898 bp, 896 bp, 249 bp.
FIG. 6B the enzymatic cleavage agarose gel electrophoregram of recombinant lentiviral plasmid pCARbcma-silencer, and lane 1 is the result of electrophoresis of 1 kb DNA ladder Marker; lane 2 is the Pvu I enzyme-digested electrophoretic result of pCAR19-silencer.

The clones were picked for colony PCR identification, and the correct clones were identified as recombinant lentiviral plasmid pCARbcma-silencer. Enzyme digestion identification was performed for the correct clones (see FIG. 6);

(13) The recombinant lentiviral plasmid pCARbcma-silencer was double digested with BspE I and EcoR I restriction enzymes. The product was electrophoresed on a 1.5% agarose gel to confirm the 10035 bp fragment V2, then such gel was recovered and placed in an Eppendorf tube. The corresponding fragments were recovered with Agarose Gel Recovery Kit of MN (see Table 1), and the purity and concentration of the product were determined;

(14) The synthesized siRNA1453-F/R-siRNA1460-F/R were dissolved into 20 μM with oligo annealing buffer respectively, and each 30 μl of the corresponding F and R were mixed. The mixture of siRNA1453-F/R-siRNA1460-F&R was heated in a water bath at 95° C. for 5 minutes, and then the water bath was opened and allowed to cool to room temperature to form double-stranded oligonucleotide fragments. Take 1 μl for the ligation reaction (see Table 4), ligate at 4° C. for 16 h, and then place it on ice for 2-3 minutes. Add the reaction solution to 50 μl of TOP10, gently rotate to mix the contents, place them on ice for 30 minutes, then put the tubes in the thermostatic water bath pre-warmed to 42° C. for 90 seconds, and quickly transfer the tubes in an ice bath. The cells were allowed to cool for 2-3 minutes. Add 900 μl of LB medium to each tube, then put the tubes to a 37° C. shaker and incubate for 1 hour to resuscitate the bacteria. Take 100 μl of transformant bacteria solution to apply to an Amp LB agar plate, invert the plate, and culture in a thermostatic incubator at 37° C. for 16 hours.

Figures 7, 8:
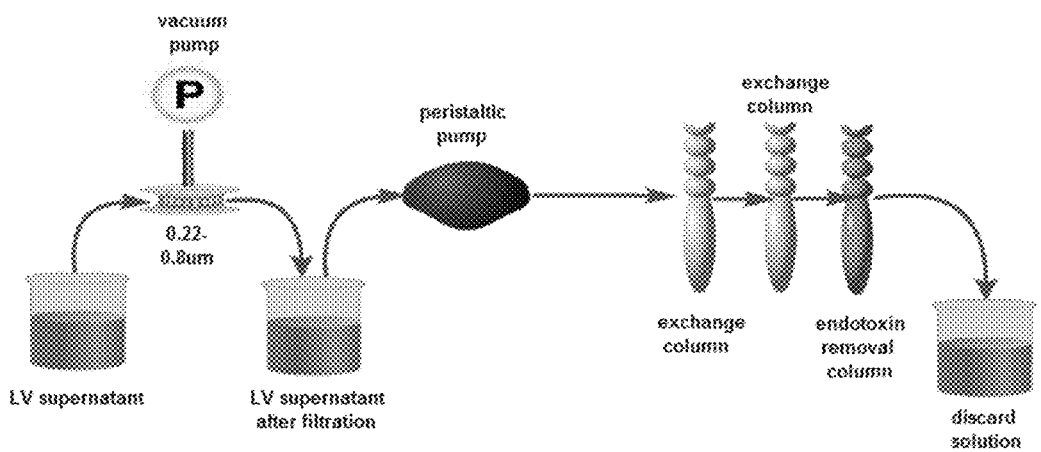
FIG. 8 is a flowchart of ion exchange chromatography for purification of recombinant lentiviral vectors.

The clones were picked for colony PCR identification, and the correct clones were identified as PD-1 knock-down recombinant lentiviral plasmids pCARbcma-1453-pCARbcma-1460. The correct clones were sequenced and identified (see FIG. 7).

TABLE 4

20 μl ligation reaction system

| Reagent | Volume (μl) |
| --- | --- |
| H₂O | 13 |
| V2 | 3 |
| 10 × T4 DNA ligase Buffer | 2 |
| T4 DNA ligase | 1 |
| Annealed double-stranded oligonucleotides | 1 |

2. Packaging of Recombinant Lentiviral Vectors lvCARbcma-1453-lvCARbcma-1460

(1) Complete medium: take out the pre-warmed fresh medium, add 10% FBS+5 ml Pen-Srep, and mix them upside down;

(2) 1×PBS solution: weigh 8 g of NaCl, 0.2 g of KCl, 3.58 g of Na₂HPO₄.12H₂O, 0.24 g of KH₂PO₄, and put them in a 1000 ml beaker, and add 900 ml of Milli-Q grade ultrapure water to dissolve. After completion of the dissolution, the volume was adjusted to 1000 ml using a 1000 ml measuring cylinder, and the mixture was sterilized by heat sterilization at 121° C. for 20 minutes; (3) 0.25% Trypsin solution: weigh 2.5 g of Trypsin, 0.19729 g EDTA, and put them in a 1000 ml beaker, and add 900 ml of 1×PBS solution to dissolve. After completion of the dissolution, the volume was adjusted to 1000 ml using a 1000 ml measuring cylinder, and the mixture was sterilized via 0.22 μM filter. It could be saved in the refrigerator at −20° C. for long-term use;

(4) 0.5M CaCl₂) solution: weigh 36.75 g of CaCl₂, and dissolve it with 400 ml of Milli-Q grade ultrapure water; The volume was adjusted to 500 ml with Milli-Q grade ultrapure water, and mixed; The mixture was sterilized via 0.22 μM filter, and stored in 50 ml centrifuge tubes with about 45 ml in each tube at 4° C.

(5) 2×HBS solution: weigh 4.09 g of NaCl, 0.269 g of Na₂HPO₄, 5.96 g of Hepes, and dissolve them with 400 ml Milli-Q grade ultrapure water; After calibrating the PH meter, the PH of the HBS solution was adjusted to 7.05 with 2M NaOH solution. It was about 3 ml of 2M NaOH to consume to adjust the PH of each bottle of HBS.

(6) The frozen HEK293T/17 cells were removed from the liquid nitrogen container and repidly transferred to a 37° C. water bath for 1-2 minutes, and then put them on a super clean bench. Aseptically transfer all the liquid in the freezing tube to a 10 cm² petri dish, and make up DMEM containing 10% FBS to 8 mL/10 cm² dish, and observe the cells under microscope after 24 hours. Passage was performed with the degree of cell confluence greater than 80%;

(7) HEK293T/17 cells with good cell status and no pollution were selected, and each 2-6 petri dishes were used as a group. After trypsinizing the cells, 4-12 ml of complete medium was pipetted with an electric pipette to add 2 ml to each digested dish to avoid drying the dish; All cells were isolated into single cell suspensions using a 1 ml pipette and transferred to medium bottles;

(8) The remaining cells in the above 2-6 petri dishes were transferred to the medium bottles, and the petri dishes were rinsed with the medium again;

(9) Close the cap of the medium bottles and turn them upside down for about 10 times to fully mixed the cell suspension. Transfer the cells to 8-24 10 cm$^2$ petri dishes. The cell density of each dish shall be about $4 \times 10^6$ cells/10 ml complete medium. In the case that the cell density was significantly different from the expected, the number of cells would be counted. Then the cells were inoculated according to the quantity of 4-10$^6$ per dish;

(10) Arrange each of the 6 petri dishes into a pile, and keep the fit between the upper and lower dishes. Shake the petri dishes left and right, back and forth several times to make cells fully spread out, and then put them into an incubator with 5% CO. The remaining cells were treated as the same;

(11) Upon Checking the passage cells, the cells shall be at 70-80% confluence, with full contour, good attachment and even distribution in petri dishes;

(12) For changing the solution, the medium was replaced with fresh complete medium with 9 ml per dish. The CO2 concentration of incubator was increased to 8%;

(13) To prepare DNA/CaCl$_2$ according to N+0.5. The amount of HEK293T/17 cell transfection plasmid per dish was used in the following ratios: recombinant lentiviral plasmid (20 μg), pPac-GP (15 μg), pPac-R (10 μg), pEnv-G (7.5 μg). Take a new 5 ml centrifuge tube, add 0.5M CaCl$_2$: 0.25 ml, recombinant lentiviral plasmid 20 μg: pPac-GP 15 μg: pPac-R 10 μg: pEnv-G 7.5 μg, supplement ultrapure water to 0.5 ml, and cover the cap to mix them fully;

(14) Take another 5 ml centrifuge tube and add 0.5 ml DNA/CaCl$_2$ solution. Open a vortex mixer, hold the upper end of the 5 ml centrifuge tube with one hand, and make the bottom of the tube contact the oscillation chamber, so that the liquid could spread on the tube wall. Take a 1 ml pipette with anther hand to suck 0.5 mL 2×HBS solution, add it into the centrifuge tube slowly and control the flow velocity. It was advisable to complete the drip in half a minute. After 2-HBS was added, it should be oscillated for another 5 seconds, and then stop oscillating. It could be directly added into the cells that need transfection;

(15) Take a dish of cells and drop 1 mL calcium transfection solution in the centrifuge tube in the dish to distribute the calcium transfection solution throughout the petri dish as much as possible;

(16) After the calcium transfection solution was added, the petri dish was marked on the cover, and put back in another incubator with 5% CO2. Make sure that the petri dish was placed horizontally, and that there were no more than 6 petri dishes in each pile. These dishes were placed in the incubator with 5% CO2 for 6-8 h;

(17) The CO$_2$ concentration of the first incubator was adjusted at 5%;

(18) The cells status was check 24 hours later. The cell confluence should be around 80-85% and in good condition. Aspirate the medium and replace 10 ml of fresh DMEM complete medium;

(19) The transfection efficiency was observed 48 hours later. Most cells were still adherent. It could be seen that more than 95% of the cells would have green fluorescence.

The supernatant of the same virus packaging was collected together, and 10 mL of fresh medium was added to the petri dish;

(20) The same virus supernatant was collected again 72 hours later. The two collections were put together, and the petri dishes were discarded; the supernatant collected at this time contained the recombinant lentiviral vectors lvCAR-bcma-1453-lvCARbcma-1460.

Embodiment 2 Concentration and Detection of Recombinant Lentivirus Vector

I. Purification of Recombinant Lentiviral Vectors by Ion Exchange Chromatography (see FIG. 8);

(1) The collected supernatant was filtered through a 0.22 μm-0.8 μm PES filter using a Thermo vacuum pump to remove impurities;

(2) 1.5M NaCl 250 mM Tris-HCl (PH6-8) was added to the supernatant at a ratio of 1:1 to 1:10

(3) Two ion exchange columns were placed in series, and they were passed through sequentially by 4 ml 1M NaOH, 4 ml 1M NaCl, 5 ml 0.15M NaCl 25 mM Tris-HCl (pH 6-8) solution;

(4) The solution obtained in step 2 was pumped into the ion exchange column with a peristaltic pump at a rate of 1-10 ml/min;

(5) After all the supernatant was passed through the column, it was washed with 10 ml of 0.15M NaCl 25 mM Tris-HCl (pH 6-8) solution;

(6) According to the sample size, 1-5 ml of 1.5M NaCl 25 mM Tris-HCl (pH 6-8) was used for elution and the eluate was collected;

(7) The eluate was divided into tubes about 25 to 50 μl each, and stored in a refrigerator with −80° C. for long-term storage;

II. Titre Determination;

(1) 293T cells were inoculated with 24-well plates. The number of cells in each well was 5×104, and the volume of medium added was 500 ul. As the growth rate of different types of cells was different, the rate of cell fusion during viral infection was 40%-60%;

(2) Three sterile EP tubes were prepared, and 90 μl fresh complete medium (high glucose DMEM+10% FBS) was added into each tube to inoculate the cells. 24 hours later, the cells in the two pores were taken and counted with a hemocytometer to determine the actual number of cells at the time of infection, denoted as N;

(3) 10 μl of the virus stock to be determined was added to the first tube. After gently mixing, 10 μl of the virus stock was added to the second tube, and then sequentially operated until the last tube; 410 μl complete medium (high glucose DMEM+10% FBS) was added into each tube, and the final volume was 500 μl;

(4) 20 hours after the infection, the cultural supernatant was removed and changed into 5001 complete medium (high glucose DMEM+10% FBS). The cells were continuously cultured for 48 hours in 5% C02;

(5) After 72 hours, the fluorescence expression was observed. Under normal circumstances, the number of fluorescence cells decreased with the increase of dilution ratio. At the same time, photos were taken;

(6) The cells were digested with 0.2 ml 0.25% trypsin-EDTA solution, and then they were placed at 37° C. for 1 minute. The whole cellular surface were purged with medium, and the cells were collected by centrifugation. Genomic DNA was extracted according to the instructions of DNeasy kit. 200 μl of eluent were added to each sample tube to remove DNA, and then they were quantified;

(7) The DNA detection qPCRmix manifold I was prepared (QPCR primer sequences were SEQ ID NO: 59-SEQ ID NO: 60):

| | |
|---|---|
| 2 × TaqMan Master Mix | 25 μl × n |
| Forward primer (100 pmol ml−1) | 0.1 μl × n |
| Reverse primer (100 pmol ml−1) | 0.1 μl × n |
| Probe (100 pmol ml−1) | 0.1 μl × n |
| H$_2$O | 19.7 μl × n | n = number of reactions. For example, the total n were 40. 1 ml of 2 × TaqMan Universal PCR Master Mix, 4 μl of forward primer, 4 μl of reverse primer, 4 μl of probe and 788 μl of H$_2$O were mixed and Placed on ice after being shaken;

(8) The reference DNA detection qPCRmix manifold II were prepared (QPCR primer sequences were SEQ ID NO: 59-SEQ ID NO: 60):

| | |
|---|---|
| 2 × TaqMan Master Mix | 25 μl × n |
| 10 × RNaseP primer/probe mix | 2.5 μl × n |
| H$_2$O | 17.5 μl × n | n = number of reactions. For example, the total n were 40. 1 ml of 2 × TaqMan Universal PCR Master Mix, 100 μl pf 10 × RNaseP primer/probe mix and 700 μl of H$_2$O were mixed and placed on ice after being shaken;

(9) The PCR system was established on a pre-cooled 96-well PCR plate. Take 45 μl from each tube of manifold I to add to the wells of each row of A-D. Take 45 μl from each tube of manifold II to add to the wells of each row of E-G.

(10) 5 μl of the standard plasmid and the genomic DNA from the samples to be tested were taken respectively to add to the A-D row, and each sample was repeated once. 1 well was left to add 5 μl of water as no-template control.

(11) 5 μl of the genomic standards and the genomic DNA from the samples to be tested were taken respectively to add to the E-G row, and each sample was repeated once. 1 well was left to add 5 μl of water as no-template control.

(12) The quantitative PCR instrument used was the ABI PRISM 7500 quantitative system. The cyclic conditions were set to: 50° C. 2 min, 95° C. 10 min, (95° C. 15 sec, 60° C. 1 min)×40 cycle.

Data analysis: the copy number of lentiviral vectors integrated in the measured DNA samples was calibrated with the number of genomes to obtain the copy number of viruses integrated in each genome.

The calculation formula of integration units per ml (IU ml$^{-1}$) was as follows:

$$IU\ ml^{-1} = (C \times N \times D \times 1000)/V$$

Of C=the average virus copy number per genome which:
   integration
   N=number of cells at the time of infection (approximately $1 \times 10^{-5}$)
   D=dilution of the viral vector
   V=the volume of diluted virus added

Figure 9:
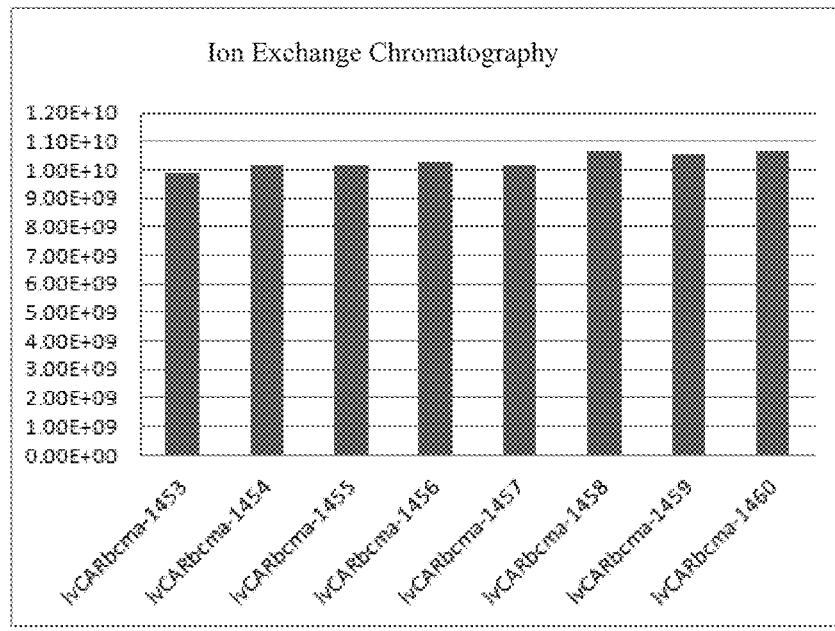
FIG. 9 shows the titer detection results of recombinant lentiviral vectors.

(13) Titer results of recombinant lentiviral vector lvCAR19-1761-lvCAR19-1769 (see FIG. 9);

III. Endotoxin Determination;

(1) The working standard of endotoxin was 15 EU per dose;

(2) Sensitivity of Tachypiens Amebocyte Lysate (TAL) λ=0.25 EU/ml, 0.5 ml/tube (3) Dilution of endotoxin standard: take one endotoxin standard, dilute it into 4× and 2× solution with BET water, seal with sealing film and vortex for 15 min; During dilution, each dilution step should be mixed on the vertex mixer for 30 s;

(4) Adding: Several TAL were taken, each was dissolved in 0.5 ml of BET water, and then divided into several exdotoxin-free tubes (0.1 ml each tube). Two of them were negative control which were added 0.1 ml of BET water to each of them;

Two tubes were positive control which were added 0.1 ml of endotoxin working standard solution with concentration of 2λ to each of them;

Two tubes were positive control of sample which were added 0.1 ml sample solution contained 2× endotoxin standard (1 ml of 20× dilution of sample to be tested+1 ml of solution contained 4× endotoxin standard=2 ml of 40× dilution of sample contained 2λ endotoxin standard).

0.1 ml of sample was added to the sample tube. The dilution ratio was in accordance with the Table 5. They were placed in water bath (or incubator) at 37±1° C. for 60±1 min;

TABLE 5

Dilution ratio of exdotoxin and corresponding endotoxin content

| | Dilution Multiple | | | | | | |
|---|---|---|---|---|---|---|---|
| | Original Fluid | 5 | 10 | 20 | 40 | 80 | 160 |
| Corresponding EU/ml Result | 0.25 | 1.25 | 2.5 | 5 | 10 | 20 | 40 |

(5) The endotoxin detection results of the recombinant lentiviral vector lvCAR19-1761-lvCAR19-1769 (as shown in Table 6) showed that the endotoxin content was between 0-2.5 EU/ml, which met the requirements;

TABLE 6

Detection results of endotoxin

| | Dilution Multiple | | | | | | |
|---|---|---|---|---|---|---|---|
| | Original Fluid | 5 | 10 | 20 | 40 | 80 | 160 |
| Corresponding EU/ml | 0.25 | 1.25 | 2.5 | 5 | 10 | 20 | 40 |
| lvCARbcma-1453 | (+) | (−) | (−) | (−) | (−) | (−) | (−) |
| lvCARbcma-1454 | (+) | (−) | (−) | (−) | (−) | (−) | (−) |
| lvCARbcma-1455 | (+) | (−) | (−) | (−) | (−) | (−) | (−) |
| lvCARbcma-1456 | (+) | (+) | (−) | (−) | (−) | (−) | (−) |
| lvCARbcma-1457 | (+) | (−) | (−) | (−) | (−) | (−) | (−) |
| lvCARbcma-1458 | (+) | (+) | (−) | (−) | (−) | (−) | (−) |
| lvCARbcma-1459 | (+) | (+) | (−) | (−) | (−) | (−) | (−) |
| lvCARbcma-1460 | (+) | (−) | (−) | (−) | (−) | (−) | (−) |

IV. Determination and Comparison of Mycoplasma;

(1) Cell samples were cultured in antibiotic-free medium three days before the experiment;

(2) 1 ml of cell suspension was collected (the number of cells is greater than $1*10^5$) to place in a 1.5 ml centrifuge tube;

(3) Centrifuge at 13000×g for 1 min, collect the precipitate, and discard the medium;

(4) 500 μl of PBS was added. The mixture was blew and sucked with a pipette or vortex oscillated to resuspend the precipitate. Centrifuge at 13000×g for 5 min;

(5) To repeat step 4 once;

(6) 50 μl of Cell Lysis Buffer was added. The mixture was blew and sucked with a pipette. After fully mixed, it was incubated in the water at 55° C. for 20 min;

(7) The sample was heated at 95° C. for 5 min;

(8) After centrifugation at 13000×g for 5 min, 5 µl of supernatant was used as a template. 25 µl PCR reaction system was: 6.5 µl of ddH$_2$O, 1 µl of Myco Mix, 12.5 µl of 2×Taq Plus Mix Master (Dye Plus), 5 µl of template; PCR circulation condition was: 95° C. 30 sec, (95° C. 30 sec, 56° C. 30 sec, 72° C. 30 sec)*30 cycle, 72° C. 5 min.

Figure 10:
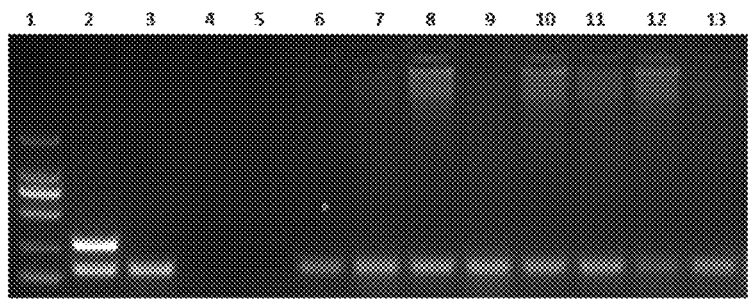
FIG. 10 shows the detection results of mycoplasma in different purification methods of recombinant lentiviral vectors. lane 1 is DL2000 marker, and the bands from top to bottom are: 2 kb, 1 kb, 750 bp, 500 bp, 250 bp, 100 bp; lane 2 is a positive control; lane 3 is a negative control; lane 4 is PBS; lane 5 is water; lane 6 is lvCARbcma-1453; lane 7 is lvCARbcma-1454; lane 8 is lvCARbcma-1455; lane 9 is lvCARbcma-1456; lane 10 is lvCARbcma-1457; lane 11 is lvCARbcma-1458; lane 12 is lvCARbcma-1459; lane 13 is lvCARbcma-1460.

(9) Detection results of mycoplasma (as shown in FIG. 10 and Table 7) showed that the recombinant lentiviral vectors lvCARbcma-1453-lvCARbcma-1460 did not contain mycoplasma.

TABLE 7

Detection results of mycoplasma

| PCR template | PCR products | Determination description |
|---|---|---|
| Positive control | 280 b and 150 bp were contained | Positive |
| | No band or only one band | Not positive |
| Negative control | 150 bp band | Negative |
| | No band or more than two bands | Not negative |
| Sample | 280 and 150 bands were contained | Contaminated by mycoplasma |
| | Only 280 band | Severely contaminated by mycoplasma |
| | Only 150 bp band | No mycoplasma contamination |
| | No band | Too few cells or PRC reaction was inhibited |

Embodiment 3 Functional Detection of Recombinant Lentivrial Vectors lvCARbcma-1453-lvCARbcma-1460

I. Detection of Cellular Level Expression of CAR Gene:

(1) After PBMC cells were infected with recombinant lentiviral vectors lvCARbcma-1453-lvCARbcma-1460 and control virus MOCK, the cells were collected. RT-PCR was used to detect the transcription level of CAR mRNA and verify the expression of CAR gene. If the transcription level of CAR mRNA increased, it indicated that the transcription level of CAR gene was successfully expressed;

(2) After PBMC cells were infected with recombinant lentiviral vectors lvCARbcma-1453-lvCARbcma-1460 and control virus MOCK, the cells were collected. Western blot was used to detect the expression level of CAR protein and verify the expression of CAR gene. If the expression level of CAR protein increased, it indicated that the translation level of CAR gene was successfully expressed;

(3) lvCARbcma-1453-lvCARbcma-1460 with MOI=15 and control virus MOCK were infected with cells respectively. After 48 h, total RNA and total protein of the cells in the 6-well plate were extracted for fluorescence quantitative PCR and western blot assay. Specific steps: four wells of the 6-well plate were coated. Relevant PBS and RN were added to each well and overnight at 4° C. After 12 hours, the virus was coated according to MOI=15, and placed the plate in an incubator at 37° C. for 5 h; Take out the 6-well plate, and discard viral supernatant. The plate was washed twice with PBS, coated with PBMC (isolated from human blood with lymphocyte separation solution) at 1*10$^6$/well, and added 500 µl of medium (containing 10% serum, 20 U/ml IL-2, Polybrene 8 ug/ml). Then such plate was allowed to stand for 20 min, centrifuge at 1000 g for 20 min at 20° C., and culture for 48 h at 37° C.

(4) The total RNA of PBMC cells in 6-well plate was extracted by Trizol method, and the cDNA was amplified by reverse transcription. QPCR primers (SEQ ID NO: 63-SEQ ID NO: 64) were used for fluorescence quantitative PCR assay (the reaction system was shown in Table 8) to verify the transcription of its mRNA with Action as its control group.

TABLE 8

20 µl qPCR reaction system

| Reagent | Volume (µl) |
|---|---|
| SYBR premix ex taq: | 10 µl |
| ROX Reverse Dye(50x) | 0.4 µl |
| Upstream primer (2.5 µM): | 0.5 µl |
| Downstream primer (2.5 µM): | 0.5 µl |
| cDNA | 1.0 µl |
| ddH$_2$O | 7.6 µl |

(5) Western Blot was used to separate the total protein extracted from PBMC by relative molecular weight by polyacrylamide gel electrophoresis. The protein was transferred to the PVDF membrane by wet transfer (4° C., 400 mA, 120 min). The PVDF membrane was blocked with a blocking solution (TBST solution containing 5% skim milk) for 1 h at room temperature. The blocking solution was diluted with Biotinylated protein L at 1:1000, and then incubated with the blocked PVDF membrane at room temperature and overnight at 4° C. The membrane was washed three times with TBST, 10 min each time. The blocking solution was diluted with the corresponding SA-HRP at 1:500, and then used to incubated PVDF membrane at room temperature for 2 h. The membrane was washed three times with TBST, 10 min each time. ECL+plus™ Western blotting system kit of Amersham was used for color development. X-ray optical development was used to obtain film showing bands.

Figure 11:
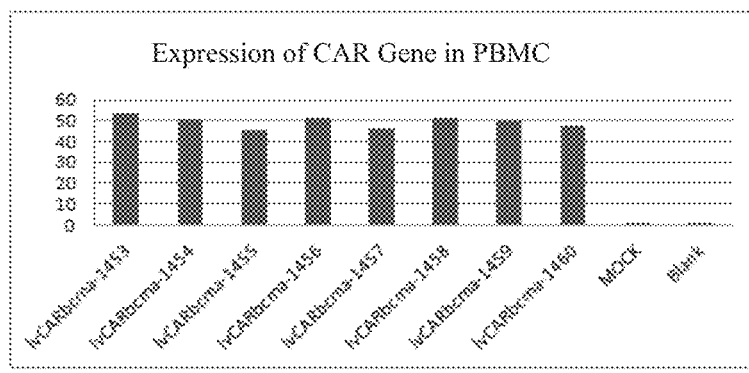
FIG. 11 is a bar chart of relative expression level of mRNA.

(6) RT-QPCR detection showed that the transcription level of CAR gene infected with PBMC by recombinant lentiviral vectors was significantly higher than that of control virus MOCK and blank cells (as shown in FIG. 11 and Table 9), indicating that the transcription level of CAR gene was successfully expressed.

TABLE 9

| Sample name | Actin (CT) | CAR (CT) | −ΔCt | −ΔΔCt | $2^{-\Delta\Delta Ct}$ |
|---|---|---|---|---|---|
| lvCARbcma-1453 | 18.94781 | 27.9884 | −9.04059 | 5.74813 | 53.74756 |
| lvCARbcma-1454 | 19.63172 | 28.76517 | −9.13345 | 5.65526 | 50.39696 |
| lvCARbcma-1455 | 19.20012 | 23.48228 | −9.28216 | 5.50655 | 45.46091 |
| lvCARbcma-1456 | 18.34099 | 27.44321 | −9.10222 | 5.6865 | 51.49997 |
| lvCARbcma-1457 | 18.2057 | 27.45988 | −9.25419 | 5.53453 | 45.35104 |

TABLE 9-continued

| Sample name | Actin (CT) | CAR (CT) | −ΔCt | −ΔΔCt | $2^{-\Delta\Delta Ct}$ |
|---|---|---|---|---|---|
| lvCARbcma-1458 | 18.31527 | 27.42907 | −9.11379 | 5.67492 | 51.08833 |
| lvCARbcma-1459 | 18.69971 | 27.8403 | −9.1406 | 5.64812 | 50.14799 |
| lvCARbcma-1460 | 19.56607 | 28.77406 | −9.20799 | 5.58073 | 47.85924 |
| MOCK | 19.75225 | 34.55302 | −14.8008 | −0.01206 | 0.991675 |
| Blank | 19.72942 | 34.51814 | −14.7887 | 0 | 1 |

Figure 12:
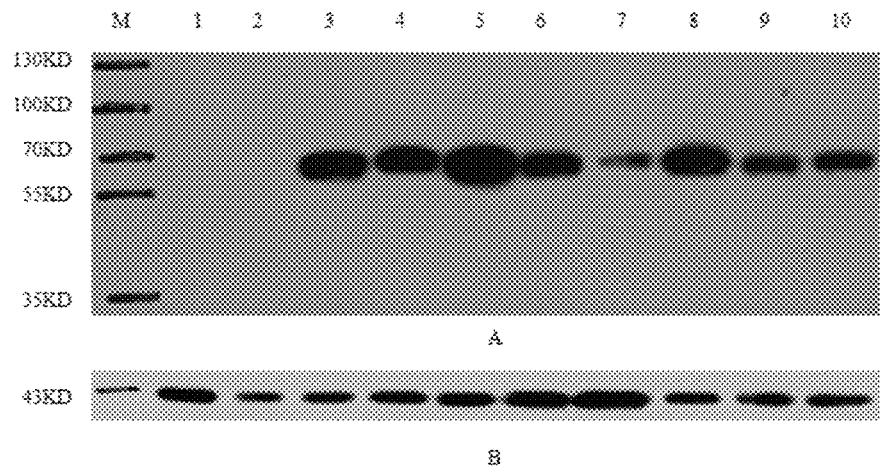
In FIG. 12 A, lane 1 is PBMC blank cells; lane 2 is the control virus MOCK; lane 3 is lvCAR-bcma-1453; lane 4 is lvCARbcma-1454; lane 5 is lvCAR-bcma-1455; lane 6 is lvCARbcma-1456; lane 7 is lvCAR-bcma-1457; lane 8 is lvCARbcma-1458; lane 9 is lvCARbcma-1459; lane 10 is lvCARbcma-1460.

(7) Western Blot results showed that the expression level of CAR protein infected with PBMC with recombinant lentiviral vectors was significantly higher than that of control virus MOCK and blank cells (as shown in FIG. 12), indicating that the translation level of CAR gene was successfully expressed.

II. Evaluation of PD-1 Knock-down Effect (PD-1mRNA Transcription Level)

(1) BCMA-K562 cells and PBMC cells were cultured separately;

(2) Four days before start of the experiment, the virus of lvCARbcma-1453-lvCARbcma-1460 with MOI=15 was infected with PBMC cells, and cultured for 72-96 h;

(3) 4×10⁵ of target cells (CD19+K562) and 2.8×10⁶ of effector cells (lvCARbcma-1453-PBMC-lvCARbcma-1460-PBMC cells) were collected, centrifuged at 800 g for 6 min, and supernatant was discarded;

(4) The target cells and effector cells were resuspended with 1 ml of 1×PBS solution respectively, centrifuged at 800 g for 6 min, and the supernatant was discarded;

(5) Step 4 was repeated once;

(6) Effector cells were resuspended with 700 μl medium (1640 medium+10% FBS), and target cells were resuspended with 2 ml medium (1640 medium+10% FBS).

(7) The experimental ports were set with the ratio of effector cells to target cells of 10:1, and the Blank group was set;

(8) Being plate centrifuged at 250×g for 5 min;

(9) They were co-cultured in an incubator with 5% C02 at 37° C. for 24 hours. 100 μl of co-cultured supernatant was collected to detect the transcriptional level of PD-1 mRNA;

(10) The total RNA of the mixed cells above was extracted by Trizol method, and the cDNA was amplified by reverse transcription. QPCR primers (SEQ ID NO: 57--SEQ ID NO: 58) were used for fluorescence quantitative PCR assay (the reaction system was shown in Table 6) to verify the transcription of its mRNA with Action as its control group.

Figure 13:
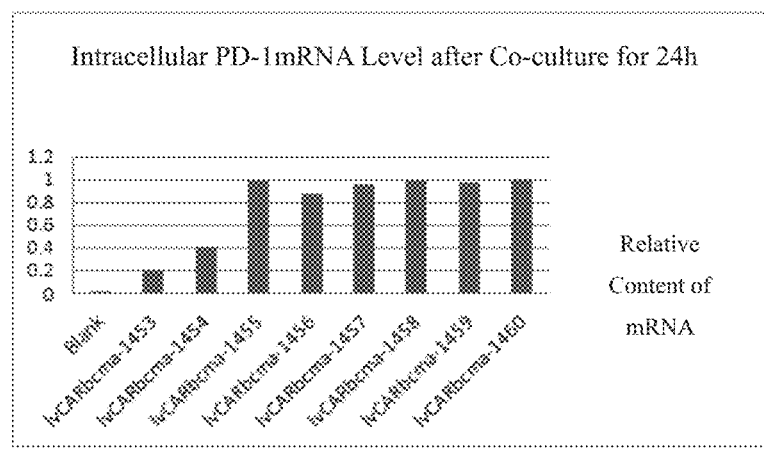
FIG. 13 shows the mRNA transcriptional level of PD-1 upon RT-QPCR test and after target cells have been incubated with CAR-T cells transduced by PD-1 knock-down recombinant lentiviral vectors lvCARbcma-1453-lvCAR-bcma-1460 for 24 h.

(11) RT-QPCR detection results showed that after a part of PBMC transduced by PD-1 knock-down recombinant lentiviral vectors were incubated with target cells, the mRNA content of PD-1 gene was significantly lower than that of control virus lvCARbcma-1460 (see FIG. 13 and Table 10), indicating PD1siRNA can knock down the transcriptional level of PD-1 gene, in which the knock-down effect of lvCARbcma-1453 was the best and reached over 70%. As Blank group is not activated by target cells, its PD-1 transcriptional level was not increased.

TABLE 10

| Sample name | Actin (CT) | PD-1 (CT) | −ΔCt | −ΔΔCt | $2^{-\Delta\Delta Ct}$ |
|---|---|---|---|---|---|
| Blank | 13.27986 | 35.211302 | −21.9314 | −7.01064 | 0.007755 |
| lvCARbcma-1453 | 13.06856 | 30.328141 | −17.2536 | −2.33878 | 0.197677 |
| lvCARbcma-1454 | 14.11226 | 30.347056 | −16.2348 | −1.314 | 0.402295 |
| lvCARbcma-1455 | 13.23032 | 28.156707 | −14.9284 | −0.00759 | 0.994752 |
| lvCARbcma-1456 | 14.93184 | 30.045561 | −15.1137 | −0.19293 | 0.874829 |
| lvCARbcma-1457 | 14.74173 | 29.710368 | −14.9686 | −0.04784 | 0.967382 |
| lvCARbcma-1458 | 14.89117 | 29.821291 | −14.9301 | −0.00933 | 0.993557 |
| lvCARbcma-1459 | 13.08795 | 28.050568 | −14.9626 | −0.04182 | 0.971426 |
| lvCARbcma-1460 | 14.17941 | 29.100206 | −14.9208 | 0 | 1 |

III. Effect Evaluation of Cell Killing Test (1) BCMA-PDL1-K562 cells and PBMC cells were cultured separately;

(2) Four days before start of the experiment, the viruses of lvCARbcma-1453-lvCARbcma-1460 with MOI=15 was infected with PBMC cells, and cultured for 72-96 h;

(3) 4×10⁵ of target cells (BCMA-PDL1-K562) and 2.8×10⁶ of effector cells (CART cells) were collected, centrifuged at 800 g for 6 min, and supernatant was discarded; (4) The target cells and effector cells were resuspended with 1 ml of 1×PBS solution respectively, centrifuged at 800 g for 6 min, and the supernatant was discarded;

(5) Step 3 was repeated once;

(6) Effector cells were resuspended with 700 μl medium (1640 medium+10% FBS), and target cells were resuspended with 2 ml medium (1640 medium+10% FBS);

(7) The experimental ports were set with the ratio of effector cells to target cells of 1:1, 5:1, 10:1, and the control group was set with 3 multiple wells each group;

(8) Being plate centrifuged at 250×g for 5 min;

(9) They were co-cultured in an incubator with 5% CO2 at 37° C. for 24 hours;

(10) Being plate centrifuged at 250×g for 5 min;

(11) 50 μl of supernatant taken from each well was added into a new 96-well plate with 50 μl of substrate solution each well (light protection operation);

(12) They were incubated in the dark for 25 min;

(13) 50 μl of TMAH was added to each well;

(14) 490 nm absorbance was detected by enzyme-labeled instrument;

(15) Average of the three multiple wells was taken: The average of median background absorbance was subtracted from the absorbance of all experimental ports, target cell wells and effector cell wells; The average of control absorbance of volume correction was subtracted from the maximum absorbance of target cells.

Figure 14:
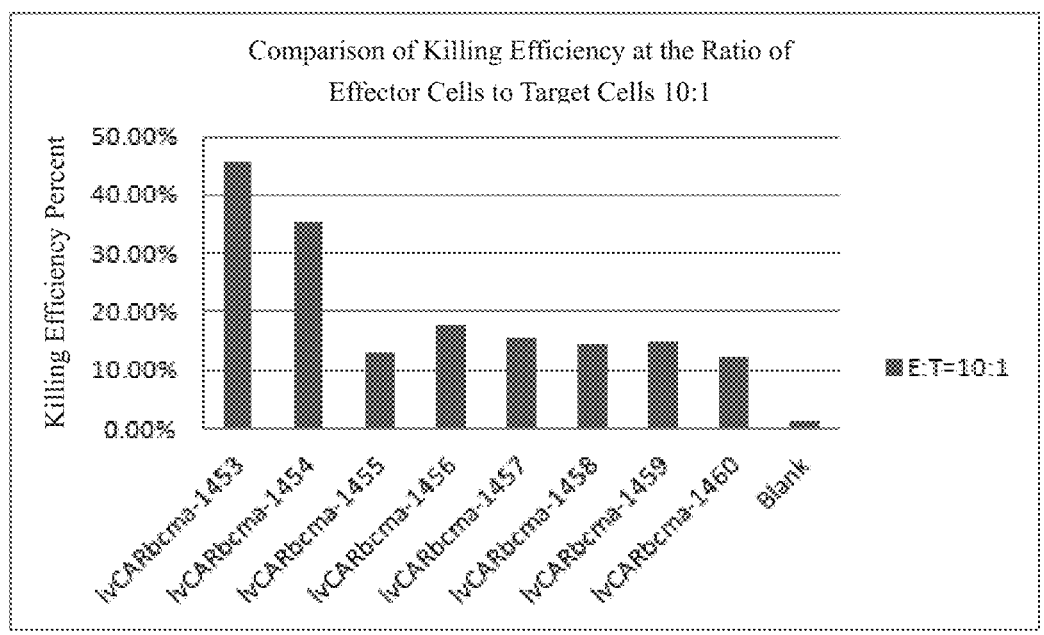
FIG. 14 shows the killing of target cells at 24 h after co-culture of different effector cells and target cells at a ratio of 10:1. E is the effector cell, and T is the target cell.

(16) The corrected values obtained in step 15 were taken into the following formula to calculate the percentage of cytotoxicity produced by each ratio of effector cells to target cells. Results as shown in FIG. 14, the killing efficiency of PD-1 knock-down recombinant lentiviral vector transduced PBMC cells was significantly higher than that of PBMC blank cells at the ratio of effector cells to target cells 10:1, in which in killing efficiency on target cells, lvCARbcma-1453-PBMC was the highest and more than 40%, the next was lvCARbcma-1454-PBMC, and the third was lvCARbcma-1455-PBMC-lvCARbcma-1458-PBMC, which was roughly same as lvCARbcma-1460-PBMC in killing efficiency on target cells; by comparing the results in FIG. 13, it can be seen that as there is PD-L1 in target cells, which transmits inhibiting signals and inhibits the immunological competence of T cells after binding to PD-1, resulting in the significant reduction in the killing efficiency of T cells on target cells. When its expression level is greatly decreased, PD-1 can effectively interfere with the activation of PD-1/PDL-1 signaling pathway, so that T cells can normally kill target cells. In the future, lvCARbcma-1453 vector and T cells transduced by it can be used clinically to the inhibit the expression level of PD-1 in CAR-T cells and reinforce the killing effect of CAR-T cells on tumor in vivo to inhibit immune escape.

Killing efficiency=(experimental ports−effector cell wells−target cell wells)/(target cell maximum well−target wells)×100%.

The better embodiments of the invention have been specified above, but the invention is not limited to the said embodiments. Technical personnel familiar with the field, without violating the spirit of the invention, make a variety of equivalent variations or substitutions, which are all included in the scope of the claim of this application.

What is claimed is:

1. An shRNA for knocking down PD-1 in a CAR T cell, wherein the shRNA comprises complementary siRNAs selected from the group consisting of
   a. SEQ ID NO: 41 and SEQ ID NO: 42;
   b. SEQ ID NO: 43 and SEQ ID NO: 44;
   c. SEQ ID NO: 45 and SEQ ID NO: 46;
   d. SEQ ID NO: 47 and SEQ ID NO: 48,
   e. SEQ ID NO: 49 and SEQ ID NO: 50;
   f. SEQ ID NO: 51 and SEQ ID NO: 52; and
   g. SEQ ID NO: 53 and SEQ ID NO: 54.

2. The shRNA of claim 1, wherein, the shRNA is an essential material in a medicine for eliminating or relieving the immune escape mechanism of tumor.

3. A recombinant expression vector comprising the shRNA of claim 1.

4. The recombinant expression vector according to claim 3, wherein the recombinant expression vector is a lentiviral expression vector, a retroviral expression vector, an adenovirus expression vector, an adeno-associated virus expression vector or a plasmid.

5. The recombinant expression vector according to claim 4, wherein, the recombinant expression vector is the lentiviral expression vector and the lentiviral expression vector comprises a prokaryotic replicon pUC Ori sequence as shown in SEQ ID NO: 2; and the recombinant expression vector comprises:
   an AmpR sequence with Ampicillin resistance gene as shown in SEQ ID NO: 1;
   a virus-replicon SV40 Ori sequence as shown in SEQ ID NO: 3;
   a lentivirus packaging cis element used for lentivirus packaging;
   a ZsGreen1 green fluorescent protein as shown in SEQ ID NO: 11;

an IRES ribosome binding sequence as shown in SEQ ID NO: 12;
a human EF1α promoter as shown in SEQ ID NO: 15;
a gene encoding an anti-BCMA chimeric antigen receptor;
an enhanced woodchuck hepatitis virus post-transcriptional regulatory element (eWPRE) as shown in SEQ ID NO: 13; and
a human RNA polymerase III promoter hU6, as shown in SEQ ID NO: 14, operably linked to the shRNA of claim 1.

6. The recombinant expression vector according to claim 5, wherein, the lentiviral expression vector comprises:
a lentivirus 5' terminal LTR as shown in SEQ ID NO: 5,
a lentivirus 3' terminal self-inactivating LTR as shown in SEQ ID NO: 6,
a Gag cis element as shown in SEQ ID NO: 7,
an RRE cis element as shown in SEQ ID NO: 8,
an env cis element as shown in SEQ ID NO: 9, and
a cPPT cis element as shown in SEQ ID NO: 10.

7. The recombinant expression vector according to claim 5, wherein, the lentiviral expression vector comprises:
a lentivirus 5' terminal LTR as shown in SEQ ID NO: 5,
a lentivirus 3' terminal self-inactivating LTR as shown in SEQ ID NO: 6,
a Gag cis element as shown in SEQ ID NO: 7,
an RRE cis element as shown in SEQ ID NO: 8,
an env cis element as shown in SEQ ID NO: 9,
a cPPT cis element as shown in SEQ ID NO: 10, and
an RSV promoter as shown in SEQ ID NO: 4.

8. The recombinant expression vector according to claim 5, wherein, the eWPRE has 6 enhanced nucleotide mutations at positions g.396G>A, g.397C>T, g.398T>C, g.399G>A, g.400A>T, and g.411A>T, as shown in SEQ ID NO: 13.

9. The recombinant expression vector according to claim 5, wherein, the anti-BCMA chimeric antigen receptor comprises:
a serialized CD8 leader chimeric receptor signal peptide, as shown in SEQ ID NO: 16,
a BCMA single-chain antibody light chain VL, as shown in SEQ ID NO: 17,
an Optimal Linker C, as shown in SEQ ID NO: 18,
a BCMA single-chain antibody heavy chain VH, as shown in SEQ ID NO; 19,
a CD8 chimeric receptor hinge, as shown in SEQ ID NO: 20,
a CD8 chimeric receptor transmembrane domain, as shown in SEQ ID NO: 21,
a CD137 chimeric receptor inducible co-stimulator, as shown in SEQ ID NO: 22, and
a TCR chimeric receptor T cell activation domain, as shown in SEQ ID NO: 23.

10. The recombinant expression vector according to claim 5, wherein, the anti-BCMA chimeric antigen receptor comprises:
a serialized CD8 leader chimeric receptor signal peptide, as shown in SEQ ID NO: 16,
a BCMA single-chain antibody light chain VL, as shown in SEQ ID NO: 17,
an Optimal Linker C, as shown in SEQ ID NO: 18,
a BCMA single-chain antibody heavy chain VH, as shown in SEQ ID NO: 19,
a CD8 chimeric receptor hinge, as shown in SEQ ID NO: 20,
a CD8 chimeric receptor transmembrane domain, as shown in SEQ ID NO: 21,
a CD28 chimeric receptor inducible co-stimulator, as shown in SEQ ID NO: 24,
a CDI 37 chimeric receptor inducible co-stimulator, as shown in SEQ ID NO: 22, and
a TCR chimeric receptor T cell activation domain, as shown in SEQ ID NO: 23.

11. A method for constructing the recombinant expression vector of claim 3, the method comprising:
(1) storing in a lentiviral skeleton plasmid pLenti-3G silencer the AmpR sequence with Ampicillin resistance gene of SEQ ID NO: 1, prokaryotic replicon pUC Ori sequence of SEQ ID NO: 2, virus-replicon SV40 Ori sequence of SEQ ID NO: 3, lentivirus packaging cis element used for lentivirus packaging, ZsGreen1 green fluorescent protein of SEQ ID NO: 11, IRES ribosome binding sequence of SEQ ID NO: 12, enhanced woodchuck hepatitis virus post-transcriptional regulatory element (eWPRE) of SEQ ID NO: 13, and human RNA polymerase III promoter hU6 of SEQ ID NO: 14;
(2) combining the human EF1α promoter of SEQ ID NO: 15 and anti-BCMA chimeric antigen receptors;
(3) cloning the shRNA of claim 1 into the recombinant lentiviral plasmid of step (2);
(4) transfecting recombinant lentiviral plasmids pCAR19-1761 and pCAR19-1769 of step (3) with lentiviral packaging plasmids pPac-GP and pPac-R and membrane protein plasmid pEnv-G, respectively into HEK293T/17 cell, and collecting a supernatant containing recombinant lentiviral vectors; and
(5) purifying recombinant lentivirus supernatant of step (4) by ion exchange modes of extraction, adsorption, and elution.

12. A pharmaceutical composition comprising the recombinant expression vector of claim 3.

13. A CAR T cell, wherein, the CAR T cell is a T lymphocyte modified by the shRNA of claim 1.

14. A pharmaceutical composition comprising the CAR T cell of claim 13.

15. A pharmaceutical composition comprising the recombinant expression vector of claim 4.

16. A pharmaceutical composition comprising the recombinant expression vector of claim 5.

17. A pharmaceutical composition comprising the recombinant expression vector of claim 6.

18. A pharmaceutical composition comprising the recombinant expression vector of claim 7.

19. A pharmaceutical composition comprising the recombinant expression vector of claim 8.

* * * * *